United States Patent
Baba

(10) Patent No.: US 10,172,524 B2
(45) Date of Patent: Jan. 8, 2019

(54) PHOTOACOUSTIC APPARATUS

(71) Applicant: CANON KABUSHIKI KAISHA, Tokyo (JP)

(72) Inventor: Yoshitaka Baba, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 526 days.

(21) Appl. No.: 14/710,365

(22) Filed: May 12, 2015

(65) Prior Publication Data

US 2015/0327770 A1 Nov. 19, 2015

(30) Foreign Application Priority Data

May 14, 2014 (JP) .................................. 2014-100851

(51) Int. Cl.
*A61B 5/00* (2006.01)

(52) U.S. Cl.
CPC .......... *A61B 5/0095* (2013.01); *A61B 5/4312* (2013.01); *A61B 5/7475* (2013.01); *A61B 5/0091* (2013.01); *A61B 2560/0475* (2013.01); *A61B 2562/046* (2013.01)

(58) Field of Classification Search
CPC .... A61B 5/0091; A61B 5/0095; A61B 5/4312
See application file for complete search history.

(56) References Cited

U.S. PATENT DOCUMENTS

| | | |
|---|---|---|
| 5,713,356 A | 2/1998 | Kruger |
| 2005/0203370 A1 | 9/2005 | Patch |
| 2009/0295941 A1 | 12/2009 | Nakajima et al. |
| 2011/0245652 A1 | 10/2011 | Oishi |
| 2012/0123260 A1 | 5/2012 | Yuki |
| 2012/0259198 A1 | 10/2012 | Nagae et al. |
| 2013/0109941 A1 | 5/2013 | Li et al. |
| 2013/0109949 A1 | 5/2013 | Li et al. |

(Continued)

FOREIGN PATENT DOCUMENTS

| | | |
|---|---|---|
| CN | 102548484 A | 7/2012 |
| CN | 102596049 A | 7/2012 |

(Continued)

OTHER PUBLICATIONS

Lihong V.Wang et al.,"Photoacoustic Tomography: In Vivo Imaging From Organelles to Organs", Science, vol. 335,1458-1462, Mar. 23, 2012.

*Primary Examiner* — Joseph M Santos Rodriguez
(74) *Attorney, Agent, or Firm* — Canon U.S.A., Inc. IP Division

(57) ABSTRACT

A photoacoustic apparatus includes a light source; a receiving element configured to receive, at a plurality of positions, a photoacoustic wave generated through irradiation of a subject with light generated by the light source, and output a time-series reception signal; a signal data obtaining unit configured to obtain information that is based on a shape of the subject, generate reception signal data by reducing a data amount of the time-series reception signal on the basis of the obtained information that is based on the shape of the subject, and store the reception signal data; and an information obtaining unit configured to obtain information about the subject on the basis of the reception signal data stored in the signal data obtaining unit.

14 Claims, 10 Drawing Sheets

(56) References Cited

U.S. PATENT DOCUMENTS

| | | | |
|---|---|---|---|
| 2013/0116536 A1* | 5/2013 | Sato | A61B 5/748 600/407 |
| 2013/0324855 A1 | 12/2013 | Lisogurski et al. | |
| 2014/0093150 A1 | 4/2014 | Zalev | |
| 2015/0182126 A1* | 7/2015 | Fukutani | A61B 5/0095 600/407 |

FOREIGN PATENT DOCUMENTS

| | | | | |
|---|---|---|---|---|
| CN | 103251378 A | 8/2013 | | |
| CN | 103260502 A | 8/2013 | | |
| CN | 103354731 A | 10/2013 | | |
| JP | 2011072567 A | 4/2011 | | |
| JP | 2012-179348 A | 9/2012 | | |
| JP | 2013052195 A | 3/2013 | | |
| JP | 2013150745 A | 8/2013 | | |
| JP | WO 2013154116 A1 * | 10/2013 | | A61B 5/7207 |
| WO | 2011039979 A1 | 4/2011 | | |
| WO | 2012014390 A2 | 2/2012 | | |
| WO | 2012108172 A1 | 8/2012 | | |
| WO | 2012/140865 A1 | 10/2012 | | |
| WO | 2012150655 A1 | 11/2012 | | |
| WO | 2013082586 A2 | 6/2013 | | |

\* cited by examiner

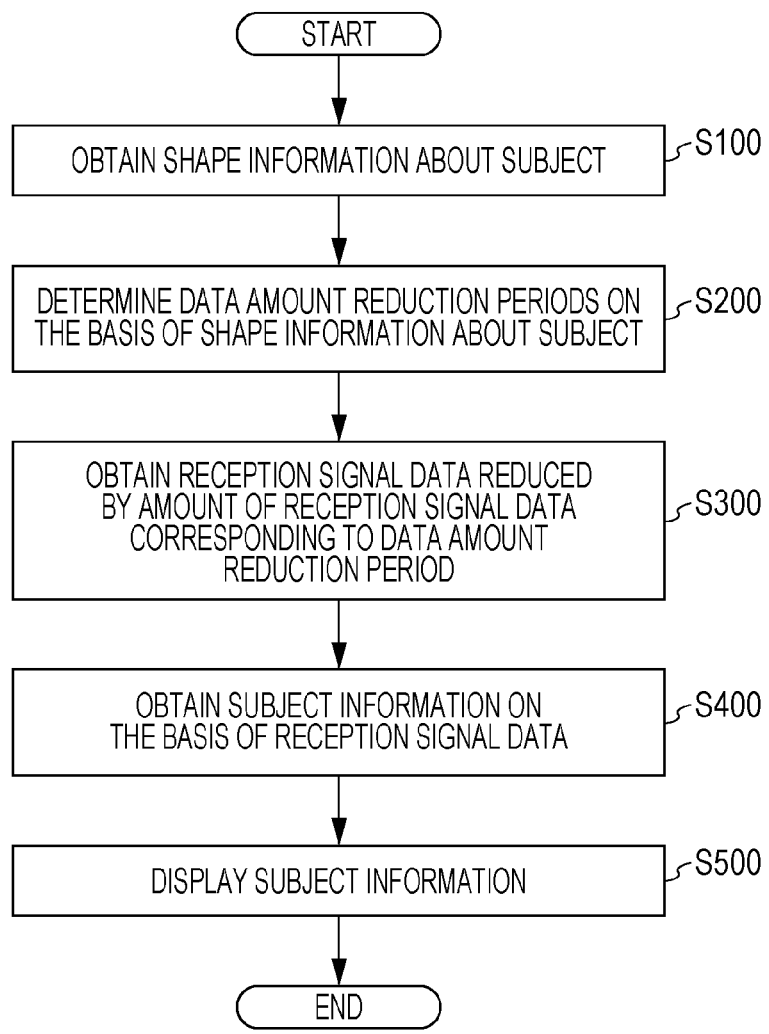

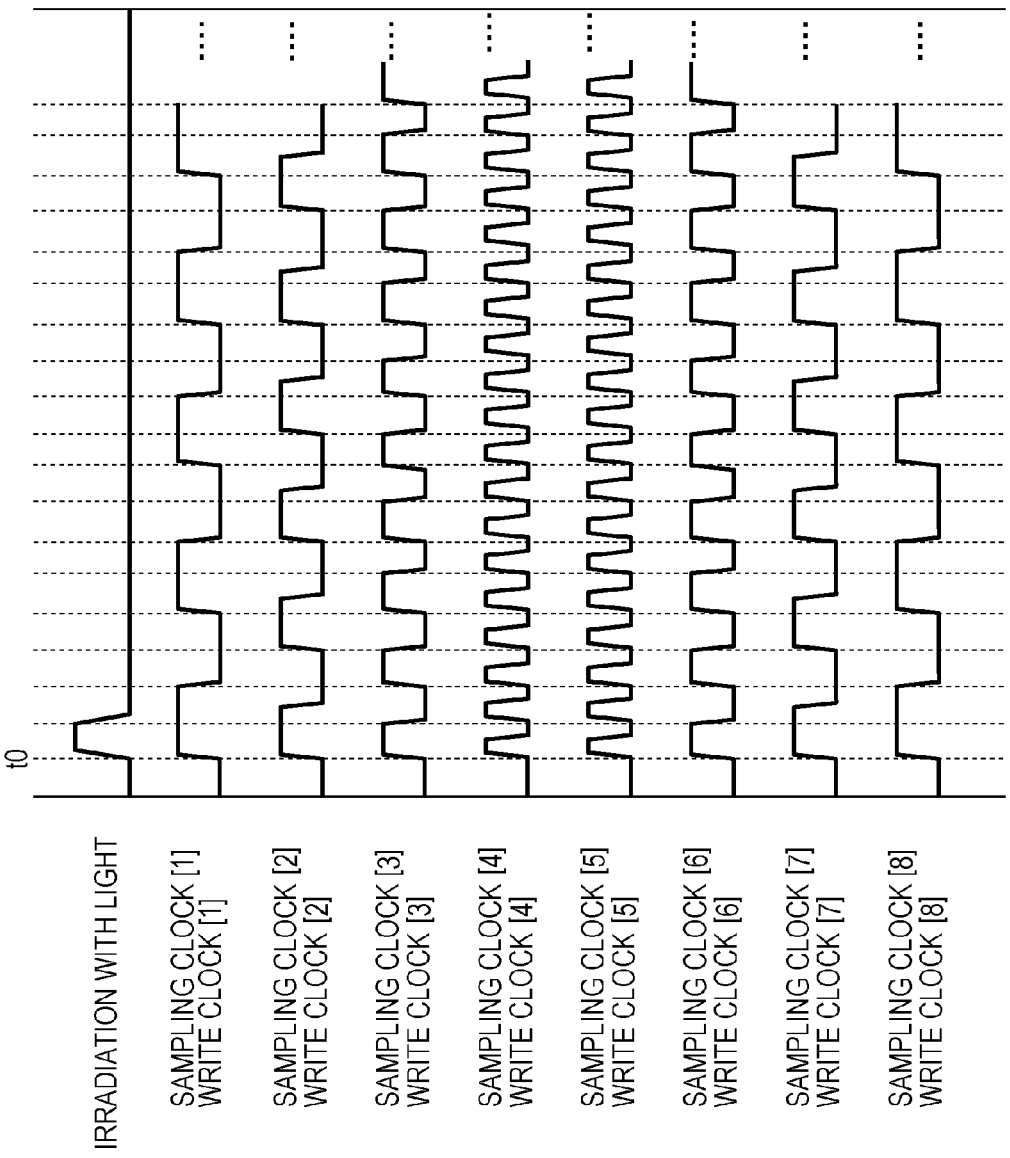

PHOTOACOUSTIC APPARATUS

BACKGROUND OF THE INVENTION

Field of the Invention

The present invention relates to a photoacoustic apparatus for obtaining subject information by using a photoacoustic effect.

Description of the Related Art

In the medical field, studies are being actively carried out into optical imaging apparatuses that irradiate a subject such as a living body with light emitted from a light source such as a laser, and convert information about the subject obtained based on incident light into an image. Photoacoustic imaging (PAI) is one of optical imaging technologies. In PAI, a subject is irradiated with pulsed light generated by a light source, acoustic waves (typically, ultrasonic waves) generated from a tissue of the subject that has absorbed energy of the pulsed light propagated and diffused in the subject are received, and an image representing subject information is generated on the basis of a reception signal of the acoustic waves.

That is, with use of a difference in absorption ratio for light energy between a subject portion such as a tumor and a tissue of another portion, elastic waves (photoacoustic waves) that are generated when the subject portion absorbs emitted light energy and instantaneously expands are received by a probe. As a result of mathematically analyzing a resulting reception signal, information about the subject, in particular, an initial sound pressure distribution, a light energy absorption density distribution, an absorption coefficient distribution, or the like can be obtained. The information is also usable for quantitative measurement of a specific substance in the subject, for example, oxygen saturation in blood. In recent years, preclinical research of imaging an angiogram of a small animal by using photoacoustic imaging and clinical research of applying this principle to diagnosis of breast cancer, or the like, have been actively carried out ("Photoacoustic Tomography: In Vivo Imaging From Organelles to Organs", Lihong V. Wang Song Hu, Science 335, 1458 (2012)).

U.S. Pat. No. 5,713,356 describes a photoacoustic apparatus that uses a probe including a plurality of transducers disposed on a hemisphere. U.S. Pat. No. 5,713,356 describes a technique of obtaining, as subject information, an initial sound pressure distribution by using a reception signal output from the probe.

In the apparatus described in U.S. Pat. No. 5,713,356, it is necessary to store reception signals output from the transducers in a memory. There is a demand for reducing the data amount of reception signals stored in the memory.

SUMMARY OF THE INVENTION

A photoacoustic apparatus disclosed in this specification includes a light source; a receiving element configured to receive, at a plurality of positions, a photoacoustic wave generated through irradiation of a subject with light generated by the light source and output a time-series reception signal; a signal data obtaining unit configured to obtain information that is based on a shape of the subject, generate reception signal data by reducing a data amount of the time-series reception signal on the basis of the obtained information that is based on the shape of the subject, and store the reception signal data; and an information obtaining unit configured to obtain information about the subject on the basis of the reception signal data stored in the signal data obtaining unit.

Further features of the present invention will become apparent from the following description of embodiments with reference to the attached drawings.

BRIEF DESCRIPTION OF THE DRAWINGS

FIG. 3 is a flowchart illustrating an operation of the photoacoustic apparatus according to the first embodiment.

FIG. 10 is a diagram illustrating a sampling sequence according to the second embodiment.

DESCRIPTION OF THE EMBODIMENTS

Figure 1:
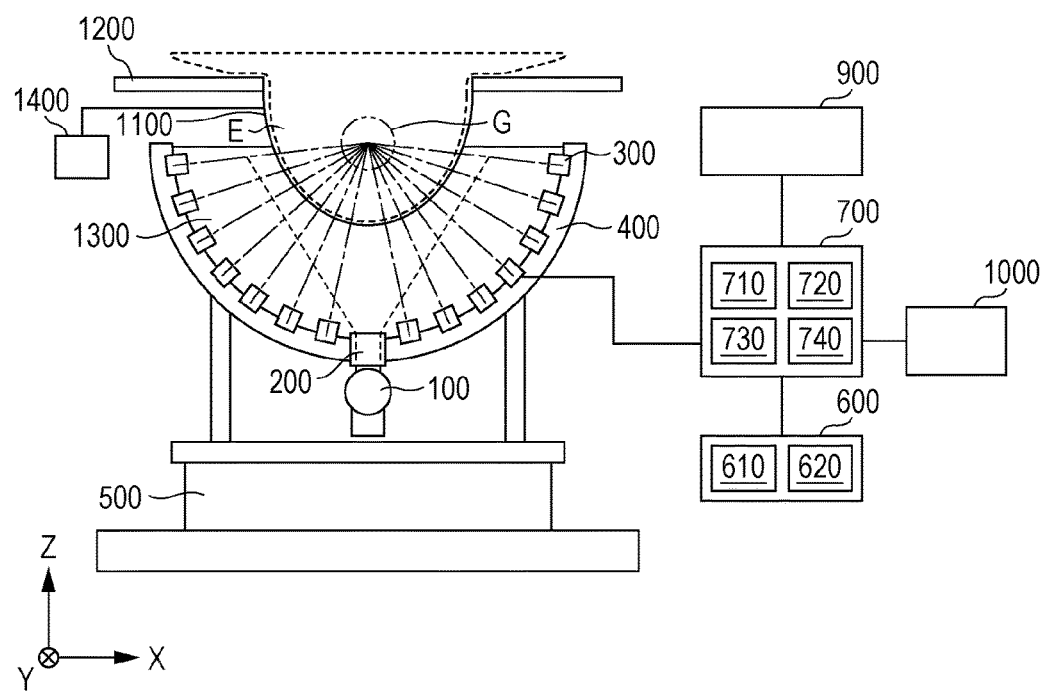
FIG. 1 is a diagram illustrating the configuration of a photoacoustic apparatus according to a first embodiment.

Hereinafter, embodiments of the present invention will be described with reference to the drawings. Each of the embodiments of the present invention described below can be implemented solely or as a combination of a plurality of the embodiments or features thereof where necessary or where the combination of elements or features from individual embodiments in a single embodiment is beneficial. Note that the dimensions, materials, shapes, relative positions, and so forth of the components described below may be appropriately changed in accordance with the configuration of an apparatus and various conditions to which the present invention is applied, and the scope of the present invention is not limited to the description given below.

For example, to obtain a high quality image by using photoacoustic imaging, it is effective to generate an image representing subject information from reception signals of photoacoustic waves that largely contribute to increased image quality.

However, regarding the reception of photoacoustic waves described in U.S. Pat. No. 5,713,356, there is a probability that photoacoustic waves that do not largely contribute to increased image quality are also received. Examples of photoacoustic waves that do not largely contribute to increased image quality include photoacoustic waves generated in a region other than a subject, and photoacoustic waves including a high-frequency component that is attenuated during propagation. If subject information is generated by using reception signals of such photoacoustic waves, increased image quality is not achieved. Further, storing of reception signals that do not largely contribute to the achievement of increased image quality in a memory causes an increase in memory capacity.

If the shape of subject is different, the relative positions of the subject and an acoustic wave receiving element may be changed, and thus the relationship between photoacoustic waves that reach the acoustic wave receiving element and contribute to increased image quality and other photoacoustic waves is also changed.

Accordingly, an embodiment of the present invention provides a photoacoustic apparatus that is capable of selectively reducing the data amount of reception signals of photoacoustic waves that do not largely contribute to increased image quality even in a case where the shape of a subject is different.

In this specification, among electric signals output from a transducer in response to receipt of photoacoustic waves, a signal that has not yet been stored in a memory in the last stage of a signal data obtaining unit is referred to as a "reception signal". Signal data that has been stored in the memory in the last stage of the signal data obtaining unit is referred to as "reception signal data".

First Embodiment

Regarding the reception of photoacoustic waves described in U.S. Pat. No. 5,713,356, photoacoustic waves generated in a region other than a subject existing between the subject and a probe may be received. Reception signals of the photoacoustic waves generated in the region other than the subject do not largely contribute to obtain subject information with a high S/N ratio in the subject. That is, with the scanning described in U.S. Pat. No. 5,713,356, in the case of obtaining reception signals for obtaining subject information, data that does not largely contribute to obtain subject information with a high S/N ratio in the subject may also be obtained.

If the shape of a subject is different, the relative positions of the acoustic wave receiving element and the subject may be changed, and thus the period in which an acoustic wave generated in a region other than the subject reaches the acoustic wave receiving element is changed.

The photoacoustic apparatus according to this embodiment changes, in accordance with the shape of a subject, a period in which the data amount of time-series reception signals is reduced. Accordingly, the data amount of reception signals of photoacoustic waves generated in a region other than a subject can be selectively reduced even if the shape of the subject is different.

If the shape of the subject is different, the relative positions of the acoustic wave receiving element and the subject may be changed. Accordingly, the relationship between a period in which photoacoustic waves derived from the subject are received and a period in which photoacoustic waves derived from a region other than the subject are received is also changed. Thus, in a case where the period in which data is reduced is not changed when the shape of the subject is changed, the data amount of reception signals of photoacoustic waves derived from the subject may be reduced.

Hereinafter, a photoacoustic apparatus according to a first embodiment will be described. FIG. 1 is a schematic diagram of the photoacoustic apparatus according to the first embodiment.

The photoacoustic apparatus illustrated in FIG. 1 obtains information representing an optical characteristic of a subject E (subject information) on the basis of reception signals of photoacoustic waves generated by a photoacoustic effect.

The subject information obtained by the photoacoustic apparatus according to this embodiment includes an initial sound pressure distribution of photoacoustic waves, a light energy absorption density distribution, an absorption coefficient distribution, and a concentration distribution of a substance forming a subject. Concentration of a substance is, for example, oxygen saturation, oxyhemoglobin concentration, deoxyhemoglobin concentration, and total hemoglobin concentration. The total hemoglobin concentration is the sum of oxyhemoglobin concentration and deoxyhemoglobin concentration.

Basic Configuration

The photoacoustic apparatus according to this embodiment includes a light source 100, an optical system 200, a plurality of acoustic wave receiving elements 300, a supporting member 400, and a scanner 500 serving as a moving unit. Further, the photoacoustic apparatus according to this embodiment includes an image capturing apparatus 600, a computer 700, a display 900 serving as a display unit, an input unit 1000, and a shape holding unit 1100. The computer 700 includes a signal data obtaining unit 710, an information obtaining unit 720, a control unit 730, and a storage unit 740.

Hereinafter, a description will be given of the configurations of the individual units of the photoacoustic apparatus and a configuration used for measurement.

Subject

The subject E is a target of measurement. A specific example of the subject E is a living body, such as a breast. Also, a phantom having a simulated acoustic characteristic and optical characteristic of a living body may be used for adjusting the apparatus. The acoustic characteristic specifically includes a propagation speed and attenuation rate of acoustic waves, and the optical characteristic specifically includes an absorption coefficient and scattering coefficient of light. Examples of a light absorber in a living body as a subject include hemoglobin, water, melanin, collagen, and fat. In the case of using a phantom, a substance having a simulated optical characteristic is sealed thereinto as a light absorber. In FIG. 1, the subject E is represented by a broken line for convenience.

Light Source

The light source 100 is a device that generates pulsed light. A laser may be used as the light source 100 to obtain large output, but a light-emitting diode or the like may be used. To effectively generate photoacoustic waves, a subject is irradiated with light for a sufficiently short time in accordance with the heat characteristic of the subject. In a case where the subject is a living body, the pulse width of pulsed light generated by the light source 100 may be several tens of nanoseconds or less. The wavelength of the pulsed light may be within the near-infrared range, which is called "biological window", for example, the range from about 700 nm to 1200 nm. The light within this range is able to reach a relatively deep portion of a living body, and thus information about the deep portion can be obtained. As for measurement of a surface portion of a living body, visible light having a wavelength from about 500 nm to 700 nm and the near-infrared range may be used. The wavelength of the pulsed light may have a high absorption coefficient relative to an observation target.

Optical System

The optical system 200 is a device that leads pulsed light generated by the light source 100 to the subject E. Specifically, the optical system 200 includes optical devices such as a lens, mirror, prism, optical fiber, diffusion plate, and so forth. In the case of leading light, the shape and optical density of the light may be changed to realize a desired light distribution by using these optical devices. The optical devices are not limited to those described above, and any other optical devices may be used as long as the above-described function is satisfied. In this embodiment, the optical system 200 is configured to illuminate a region of the curvature center of a hemisphere.

Regarding the intensity of light that is permitted to be applied to a living tissue, maximum permissible exposure (MPE) is defined by the following safety standard (IEC 60825-1: Safety of laser products, JIS C 6802: Safety standard for laser products, FDA: 21CFR Part 1040.10, ANSI Z136.1: Laser Safety Standards, and so forth). The MPE specifies the intensity of light that is permitted to be applied per unit area. Thus, a large amount of light can be led to the subject E by simultaneously irradiating a wide area of the surface of the subject E with light, and thus photoacoustic waves can be received with a high S/N ratio. For this purpose, as indicated by the broken line in FIG. 1, light may be spread over a certain area by collecting the light by using a lens.

Acoustic Wave Receiving Element

The acoustic wave receiving elements 300 are elements that receive photoacoustic waves and convert them into electric signals. The acoustic wave receiving elements 300 may have high reception sensitivity for photoacoustic waves applied from the subject E and may be applicable to a wide frequency band.

The acoustic wave receiving elements 300 may be formed of a piezoelectric ceramic material represented by lead zirconate titanate (PZT), a high polymer piezoelectric film material represented by polyvinylidene fluoride (PVDF), or the like. An element other than a piezoelectric element may be used. For example, an electrostatic capacitive element such as a capacitive micro-machined ultrasonic transducer (cMUT), an acoustic wave receiving element using a Fabry-Perot interferometer, or the like may be used.

Typically, an acoustic wave receiving element has the following reception sensitivity characteristic. That is, the reception sensitivity is the highest for incidence on a receiving surface from a normal line direction, and the reception sensitivity decreases as the incidence angle increases. A maximum value of reception sensitivity is represented by S, and the incidence angle in a case where the reception sensitivity is half of S (S/2) is represented by a. In this embodiment, a region where photoacoustic waves enter the reception surface of the acoustic wave receiving element 300 at the incidence angle $\alpha$ or less is regarded as a highly-sensitive reception region. In FIG. 1, the directions in which the reception sensitivity is the highest in the individual acoustic wave receiving elements 300 are represented by dot-and-dash lines. In this specification, an axis along the direction in which the reception sensitivity is the highest is also referred to as a "directional axis".

Supporting Member

The supporting member 400 is a substantially hemispherical container. The inner surface of the hemisphere is provided with the plurality of acoustic wave receiving elements 300, and the bottom portion (pole) of the hemisphere is provided with the optical system 200. The inner side of the hemisphere is filled with an acoustic matching material 1300 (described below).

The supporting member 400 may be formed of a metallic material having a high mechanical strength to support these elements.

In this embodiment, the supporting member 400 supports the plurality of acoustic wave receiving elements 300. The plurality of acoustic wave receiving elements 300 provided on the supporting member 400 have different reception directions, and are arranged in an array on the hemisphere surface toward the curvature center of the hemisphere. FIG. 1 is a cross-sectional view taken along the central axis of the hemispherical supporting member 400. The dot-and-dash lines that converge in a region of the subject E indicate the reception directions of the acoustic wave receiving elements 300. That is, the supporting member 400 supports the plurality of acoustic wave receiving elements 300 such that the directional axes of at least some of the plurality of acoustic wave receiving elements 300 converge.

In this way, the plurality of acoustic wave receiving elements 300 are arranged on the supporting member 400 so as to be able to receive photoacoustic waves generated in a specific region with high sensitivity. In this embodiment, the specific region is referred to as a "highly-sensitive region".

In a case where the plurality of acoustic wave receiving elements 300 are arranged in this manner, in subject information obtained by using reception signals with the method described below, the resolution is high at the curvature center of the hemisphere, and the resolution decreases as the distance from the center increases. In this embodiment, a highly-sensitive region is a region from a point of the highest resolution to a point of half the highest resolution. A region G defined by a dot-dot-dash line in FIG. 1 corresponds to the highly-sensitive region.

The directional axes of the individual acoustic wave receiving elements 300 need not cross one another as long as a desired highly-sensitive region can be formed. Also, it is sufficient that the directional axes of at least some of the plurality of acoustic wave receiving elements 300 supported by the supporting member 400 converge in the specific region so that photoacoustic waves generated in the specific region can be received with high sensitivity. That is, it is sufficient that at least some of the plurality of acoustic wave receiving elements 300 are arranged on the supporting member 400 so as to be able to receive photoacoustic waves generated in the highly-sensitive region with high sensitivity. For example, 95% or more of the plurality of acoustic wave receiving elements 300 may be arranged on the supporting member 400 so as to be able to receive photoacoustic waves generated in the highly-sensitive region with high sensitivity.

Scanner

The scanner 500 is a device for changing the relative position of the supporting member 400 with respect to the subject E by moving the position of the supporting member 400 in the X, Y, and Z directions illustrated in FIG. 1. For this purpose, the scanner 500 includes a guide mechanism for the X, Y, and Z directions, a drive mechanism for the X, Y, and Z directions, and a position sensor for detecting the position of the supporting member 400 in the X, Y, and Z directions (not illustrated). As illustrated in FIG. 1, the supporting member 400 is mounted above the scanner 500, and thus a linear guide resistant to a heavy load may be used as the guide mechanism. As the drive mechanism, a lead screw mechanism, a link mechanism, a gear mechanism, a hydraulic mechanism, or the like may be used. A motor may be used as a driving force. As the position sensor, a potentiometer including an encoder, a variable resistor, and so forth may be used.

In an embodiment of the present invention, it is sufficient that the relative positions of the subject E and the supporting member 400 is changed, and thus the supporting member 400 may be fixed and the subject E may be moved. In the case of moving the subject E, a supporting member for supporting the subject E (not illustrated) may be moved to move the subject E. Both of the subject E and the supporting member 400 may be moved.

The scanner 500 is not limited to the one for changing the relative positions of the subject E and the supporting member 400 in a three-dimensional manner, but may change the relative positions in a one-dimensional or two-dimensional manner.

The movement may be continuously performed, or may be repeatedly performed at a certain interval. The scanner 500 may be an electric-powered stage, or may be a manually-operated stage. The scanner 500 is not limited to the one described above, and any types of scanner may be used as long as it is configured to be able to move at least one of the subject E and the supporting member 400.

Image Capturing Apparatus

The image capturing apparatus 600 generates image data of the subject E and outputs the generated image data to the computer 700. The image capturing apparatus 600 includes an image capturing device 610 and an image generating unit 620. The image generating unit 620 generates image data of the subject E by analyzing a signal output from the image capturing device 610, and stores the generated image data in the storage unit 740 of the computer 700.

For example, an optical image capturing device such as a charge-coupled device (CCD) sensor or a complementary metal-oxide semiconductor (CMOS) sensor may be used as the image capturing device 610. Also, a piezoelectric element or an acoustic image capturing device for transmitting and receiving acoustic waves, such as a capacitive micromachined ultrasonic transducer (CMUT), may be used as the image capturing device 610. Some of the plurality of acoustic wave receiving elements 300 may be used as the image capturing device 610. Any other device may be used as the image capturing device 610 as long as the image generating unit 620 is able to generate an image of a subject on the basis of a signal output from the image capturing device 610.

The image generating unit 620 includes a device, such as a central processing unit (CPU), a graphics processing unit (GPU), or an analog-to-digital (A/D) converter, and a circuit, such as a field-programmable gate array (FPGA), or an application specific integrated circuit (ASIC). The computer 700 may function as the image generating unit 620. That is, an arithmetic unit of the computer 700 may be used as the image generating unit 620.

The image capturing apparatus 600 may be provided separately from the photoacoustic apparatus.

Computer

The computer 700 includes the signal data obtaining unit 710, the information obtaining unit 720, the control unit 730, and the storage unit 740.

The signal data obtaining unit 710 converts time-series reception signals output from the plurality of acoustic wave receiving elements 300 into digital signals, and stores the digital signals as reception signal data.

The information obtaining unit 720 generates subject information on the basis of the reception signal data stored in the signal data obtaining unit 710. The reception signal data is time-series signal data, and the subject information is spatial two-dimensional data or three-dimensional data. The spatial two-dimensional data is also referred to as pixel data, and the spatial three-dimensional data is also referred to as voxel data or volume data.

For example, as an image reconstruction algorithm for obtaining subject information, reverse projection in a time domain or Fourier domain usually used in a tomography technology may be used. In a case where a lot of time can be used for reconstruction, an image reconstruction method, such as an inverse problem analysis method using repetition processing, may be used.

Figure 2:
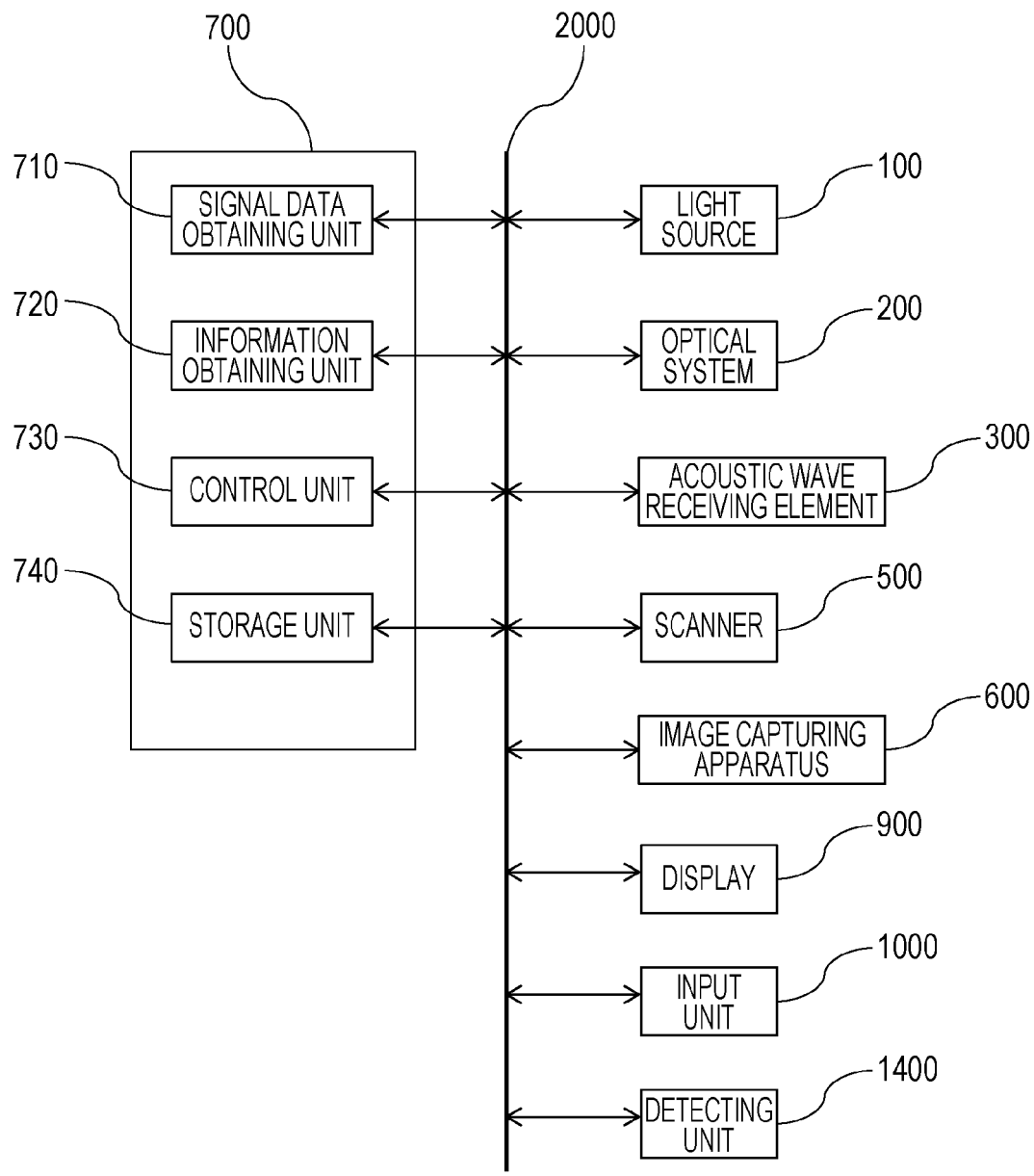
FIG. 2 is a diagram illustrating the connection between a computer and the other components according to the first embodiment.

The control unit 730 is able to control the operations of the individual units constituting the photoacoustic apparatus via a bus 2000, as illustrated in FIG. 2. The control unit 730 is typically constituted by a CPU. When the control unit 730 reads a program for controlling operations stored in the storage unit 740, the operation of the photoacoustic apparatus is controlled. The storage unit 740 that stores the program is a non-transitory recording medium.

The signal data obtaining unit 710 and the information obtaining unit 720 each include an arithmetic unit and a storage unit. The arithmetic unit is constituted by an arithmetic element, such as a CPU, a GPU, or an AD converter, and an arithmetic circuit, such as an FPGA or an ASIC. The arithmetic unit may be constituted by a plurality of elements or circuits, instead of a single element or circuit. Each processing operation according to an embodiment of the present invention may be performed by any element or circuit. The storage unit is constituted by a storage medium, such as a read only memory (ROM), a random access memory (RAM), or a hard disk. The storage unit may be constituted by a plurality of storage media, instead of a single storage medium.

In this specification, a description will be given for convenience under the assumption that the signal data obtaining unit 710, the information obtaining unit 720, the control unit 730, and the storage unit 740 are different units. Alternatively, a common element may have the functions of the individual units. For example, a certain arithmetic unit may perform arithmetic processing operations that are originally performed by the signal data obtaining unit 710, the information obtaining unit 720, and the control unit 730.

The computer 700 may be configured to be able to simultaneously perform pipeline processing on a plurality of signals. Accordingly, the time to obtain subject information can be shortened.

Acoustic Matching Material

The acoustic matching material 1300 is used to fill the space between the subject E and the acoustic wave receiving elements 300 and acoustically couple the subject E and the acoustic wave receiving elements 300. In this embodiment, the acoustic matching material 1300 is also placed between the shape holding unit 1100 and the subject E.

The acoustic matching material 1300 may also be placed between the acoustic wave receiving elements 300 and the shape holding unit 1100. Further, different types of acoustic matching materials may be placed between the acoustic wave receiving elements 300 and the shape holding unit 1100 and between the shape holding unit 1100 and the subject E.

The acoustic matching material 1300 may be a material in which photoacoustic waves are less likely to be attenuated. The acoustic matching material 1300 may be a material whose acoustic impedance is close to the acoustic impedance of the subject E and the acoustic wave receiving elements 300. The acoustic matching material 1300 may be a material having an intermediate acoustic impedance of the subject E and the acoustic wave receiving elements 300. The acoustic matching material 1300 may be a material that transmits pulsed light generated by the light source 100. The acoustic matching material 1300 may be liquid. Specifically, water, castor oil, gel, or the like may be used as the acoustic matching material 1300.

The acoustic matching material 1300 may be provided separately from the photoacoustic apparatus according to the embodiment of the present invention.

Display

The display 900 is a device that displays subject information output from the computer 700 in the form of a distribution image, numeric data, or the like. Typically, a liquid crystal display or the like is used as the display 900, but another type of display, such as a plasma display, an organic electroluminescence (EL) display, or a field emission display (FED), may be used. The display 900 may be provided separately from the photoacoustic apparatus according to the embodiment of the present invention.

Input Unit

The input unit 1000 is a member configured to enable a user to designate desired information to input the desired information to the computer 700. A keyboard, a mouse, a touch panel, a dial, a button, and the like may be used as the input unit 1000. In the case of using a touch panel as the input unit 1000, the display 900 may be a touch panel also functioning as the input unit 1000. The input unit 1000 may be provided separately from the photoacoustic apparatus according to the embodiment of the present invention.

Shape Holding Unit

The shape holding unit 1100 is a member for holding the shape of the subject E constant. The shape holding unit 1100 is attached to an attachment unit 1200. In a case where a plurality of shape holding units are used to hold the subject E in a plurality of shapes, the attachment unit 1200 may be configured so that the plurality of shape holding units can be attached thereto. In other words, a plurality of shape holding units 1100 may be provided, where each of the plurality of shape holding units 1100 has a different shape such that each of the shape holding units 1100 is capable of holding the shape of a differently shaped subject E. Thus, a plurality of differently shaped subjects E can be accommodated by selection of an appropriate shape holding unit 1100 from the plurality of shape holding units 1100.

In the case of irradiating the subject E with light via the shape holding unit 1100, the shape holding unit 1100 may be transparent with respect to the light. For example, polymethylpentene, polyethylene terephthalate, or the like may be used as the material of the shape holding unit 1100.

In a case where the subject E is a breast, the shape holding unit 1100 may have a shape formed by cutting a sphere along a certain cross section, in order to suppress deformation of the breast and hold the shape constant. The shape of the shape holding unit 1100 can be appropriately designed in accordance with the volume of a subject and a desired shape of the subject being held. The shape holding unit 1100 may be configured to fit the outer shape of the subject E so that the shape of the subject E becomes almost the same as the shape of the shape holding unit 1100. The photoacoustic apparatus may perform measurement without using the shape holding unit 1100.

Operation of Photoacoustic Apparatus

Next, a description will be given of a method for selectively storing, in a memory, photoacoustic waves generated in a subject on the basis of shape information about the subject, with reference to the flowchart illustrated in FIG. 3.

S100: Step of Obtaining Shape Information about Subject

First, the subject E is inserted into the shape holding unit 1100, and the space between the supporting member 400 and the shape holding unit 1100 and the space between the shape holding unit 1100 and the subject E are filled with the acoustic matching material 1300.

Subsequently, a reduction data determining unit 711 of the signal data obtaining unit 710 obtains information that is based on the shape of the subject E. In the embodiment of the present invention, "information that is based on the shape of the subject" is information representing the position coordinates of the surface of the subject E or information representing the type of the shape holding unit 1100. "Obtain information that is based on the shape of the subject E" means that the reduction data determining unit 711 receives information that is based on the shape of the subject E.

Hereinafter, a description will be given of a method for obtaining, with the reduction data determining unit 711, information that is based on the shape of the subject.

Figure 5:
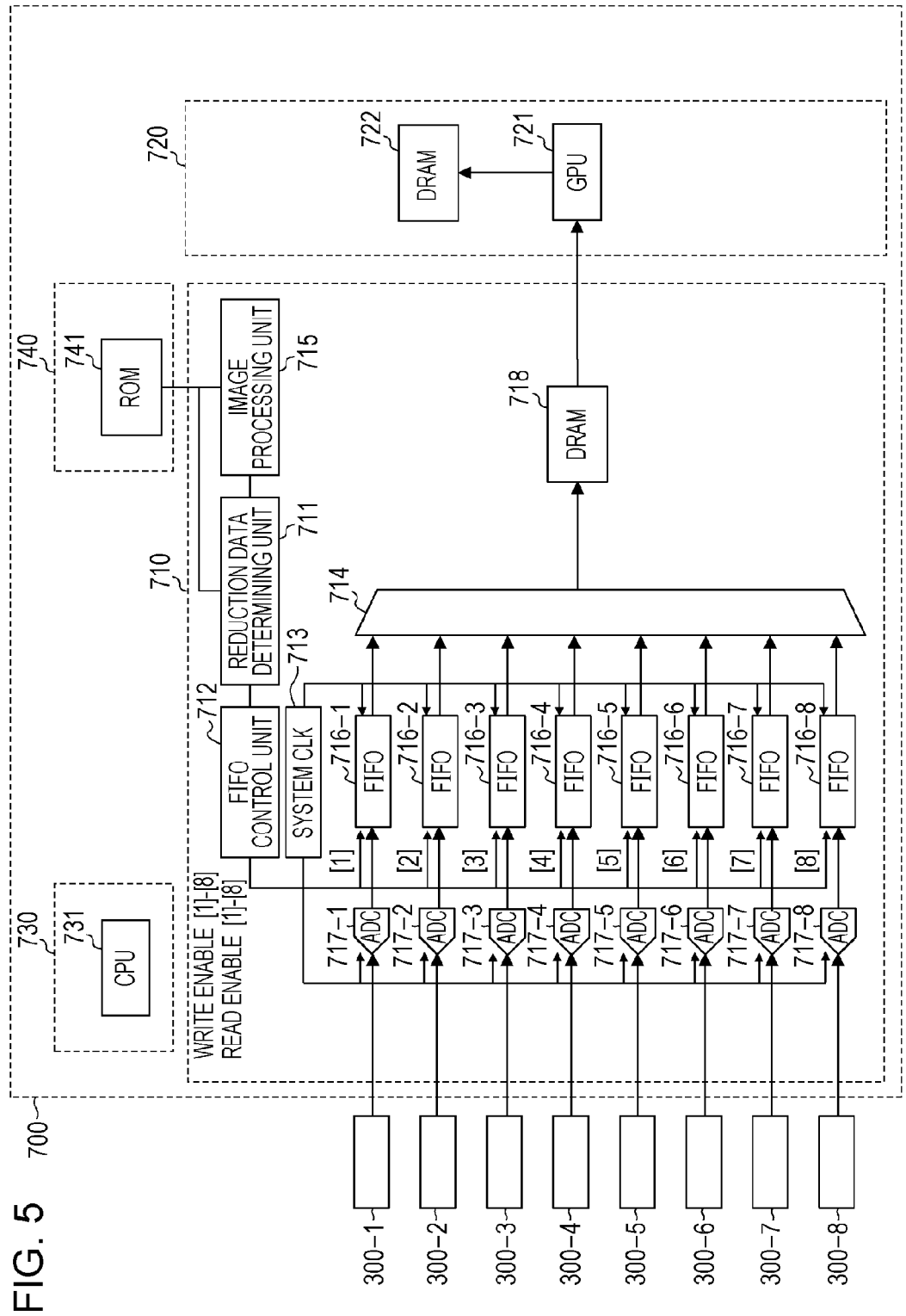
FIG. 5 is a diagram illustrating the details of the computer according to the first embodiment.

First, an image processing unit 715 reads, from a ROM 741 serving as the storage unit 740, image data of the subject E obtained by the image capturing apparatus 600 (see FIG. 5). Subsequently, the image processing unit 715 calculates coordinate information about the surface of the subject E on the basis of the image data of the subject E, and outputs the coordinate information to the reduction data determining unit 711. For example, the image processing unit 715 may calculate the coordinate information about the surface of the subject E by using a three-dimensional measurement technique, such as a stereo method, on the basis of a plurality of pieces of image data. Accordingly, the reduction data determining unit 711 is able to receive information representing the position coordinates of the surface of the subject E output from the image processing unit 715, and obtain the information as shape information about the subject E.

Alternatively, information representing the position coordinates of the surface of the shape holding unit 1100 known in advance may be stored in the ROM 741. In this case, the reduction data determining unit 711 is able to read, from the ROM 741, the information representing the position coordinates of the surface of the shape holding unit 1100, and obtain the read information as information representing the position coordinates of the surface of the subject E.

Alternatively, a detecting unit 1400 that detects the type of a shape holding unit attached to the attachment unit 1200 and outputs information representing the type of the shape holding unit to the computer 700 may be provided. In this case, the reduction data determining unit 711 is able to receive the information representing the type of the shape holding unit output from the detecting unit 1400, and obtain the information as information that is based on the shape of the subject. For example, a reader for reading an ID chip, attached to the shape holding unit 1100, representing the type of the shape holding unit 1100 may be adopted as the detecting unit 1400. Accordingly, information that is based on the shape of the subject can be obtained without performing calculation.

Alternatively, a user may input information representing the type of the shape holding unit to be used by using the input unit 1000, and the input unit 1000 may output the input information to the reduction data determining unit 711. Accordingly, the reduction data determining unit 711 is able to receive the information representing the type of the shape holding unit output from the input unit 1000, and obtain the information as information that is based on the shape of the subject. Accordingly, the information that is based on the shape of the subject can be obtained without performing calculation.

In a case where the type of the shape holding unit does not change and it is not assumed that the size of the shape holding unit changes in view of the specifications of the apparatus, the information that is based on the shape of the subject used by the reduction data determining unit 711 may be constant.

In a case where the photoacoustic apparatus performs measurement a plurality of times, information that is based on the shape of the subject and that has been obtained through this step may be used in the following measurement. In a case where the photoacoustic apparatus performs measurement a plurality of times, this step may be performed at an arbitrary timing, for example, this step may be performed for every measurement, or this step may be performed for every several measurements.

As a result of performing this step for every measurement, even if the shape of the subject differs among measurements, the following step can be performed each time on the basis of the information that is based on a correct shape of the subject.

S200: Step of Determining Data Amount Reduction Periods on the Basis of Shape Information about Subject Subsequently, the signal data obtaining unit 710 determines, on the basis of the information that is based on the shape of the subject E obtained in step S100, periods in which acoustic waves generated in a region other than the subject E reach the acoustic wave receiving elements 300. The period is regarded as a period in which the amount of reception signal data is reduced. Hereinafter, the period in which the amount of reception signal data is reduced is referred to as a "data amount reduction period", and a spatial region corresponding to this period is referred to as a "data amount reduction region".

Figure 4A:
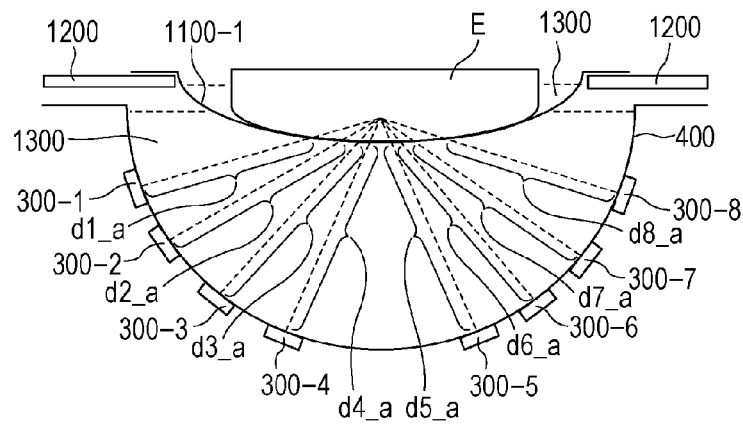
FIGS. 4A, 4B, and 4C are diagrams illustrating measurement states according to the first embodiment.
Figure 4B:
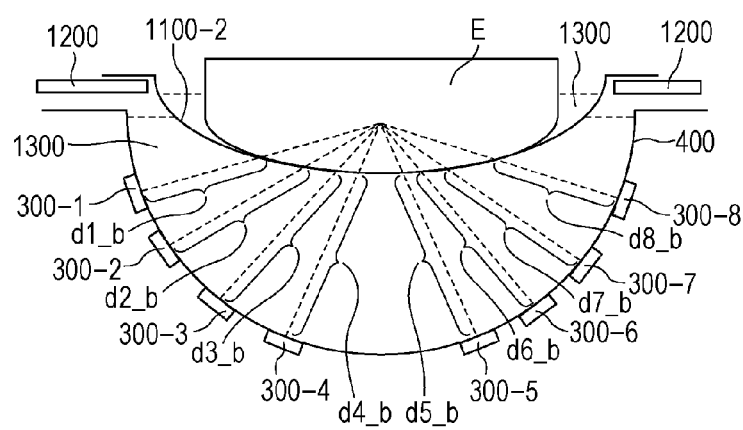
Figure 4C:
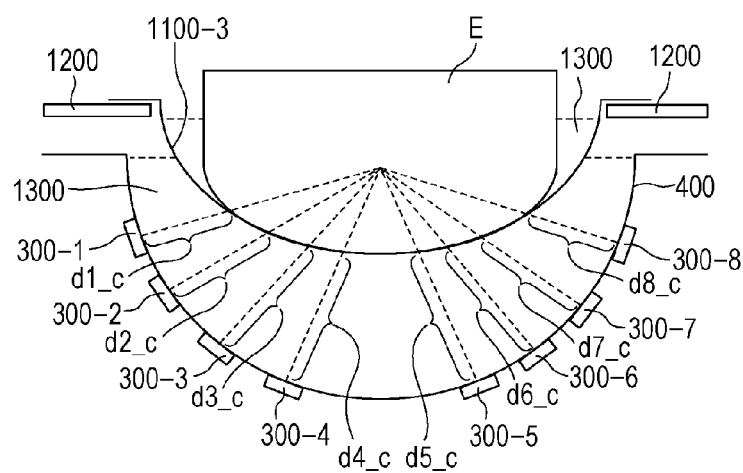

A specific example of a method for determining a data amount reduction period will be described with reference to FIGS. 4A to 4C and FIG. 5. FIGS. 4A to 4C are diagrams illustrating a case where the dimension of the shape holding unit is changed in a case where the supporting member 400 is located at a certain position. FIG. 5 illustrates a specific example of the configuration of the computer 700.

In the photoacoustic apparatus according to the embodiment, the dimension of a shape holding unit can be changed in accordance with the size of the subject E. For example, a shape holding unit 1100-1 having a small size illustrated in FIG. 4A is used in a case where the subject E has a size smaller than a standard size. A shape holding unit 1100-2 having a medium size illustrated in FIG. 4B is used in a case where the subject E has the standard size. A shape holding unit 1100-3 having a large size illustrated in FIG. 4C is used in a case where the subject E has a size larger than the standard size.

In this embodiment, a case where information based on the shapes of the individual shape holding units 1100-1 to 1100-3 is stored in the ROM 741 in advance is discussed. First, in step S100, a user inputs information representing the type of the shape holding unit to be used by using the input unit 1000. Subsequently, the reduction data determining unit 711 reads, from the ROM 741, information based on the shape of the shape holding unit on the basis of the input information, and obtains the read information as information that is based on the shape of the subject E.

The space between a plurality of acoustic wave receiving elements 300-1 to 300-8 and the shape holding unit 1100 is filled with the acoustic matching material 1300 capable of transmitting acoustic waves. However, a reception signal of photoacoustic waves generated in the part of the acoustic matching material 1300 does not largely contribute to a high S/N ratio of a reconstruction image of a subject, and thus the part of the acoustic matching material 1300 is a region for which it is not necessary to obtain reception data, that is, a data amount reduction region. In the case of FIG. 4A, the portions corresponding to distances $d1\_a$ to $d8\_a$ between the plurality of acoustic wave receiving elements 300-1 to 300-8 and the shape holding unit 1100-1 correspond to data amount reduction regions.

Thus, the reduction data determining unit 711 receives the information that is based on the shape of the subject E from the ROM 741, and determines the data amount reduction periods corresponding to the plurality of acoustic wave receiving elements 300-1 to 300-8 on the basis of the information that is based on the shape of the subject E.

For example, upon receiving position coordinate information about the surface of the subject E as the information that is based on the shape of the subject E, the reduction data determining unit 711 calculates the distances $d1\_a$ to $d8\_a$ by using the position coordinates of the surface of the subject E and the position coordinates of the plurality of acoustic wave receiving elements 300. Subsequently, the reduction data determining unit 711 divides the distances $d1\_a$ to $d8\_a$ by a sonic speed in the acoustic matching material 1300, and thereby obtains results as data amount reduction periods corresponding to the plurality of acoustic wave receiving elements 300.

Also, a case where the reduction data determining unit 711 receives information about the distances $d1\_a$ to $d8\_a$ as the information that is based on the shape of the subject E is discussed. In this case, the reduction data determining unit 711 divides the distances $d1\_a$ to $d8\_a$ by a sonic speed in the acoustic matching material 1300, and thereby obtains results as data amount reduction periods corresponding to the plurality of acoustic wave receiving elements 300.

Typically, the arrangement of the plurality of acoustic wave receiving elements 300 is known in advance, and thus the position coordinate information about the individual elements can be stored in the ROM 741 in advance. Thus, the reduction data determining unit 711 is able to use the position coordinate information about the individual elements to calculate the distances by reading the information from the ROM 741.

Typically, the shape of the shape holding unit 1100 is also known in advance, and thus the data amount reduction periods corresponding to the individual shapes (individual types) of the shape holding unit 1100 can be calculated in advance and stored in the ROM 741. That is, in the case of receiving information about the type of the shape holding unit 1100 as the information that is based on the shape of the subject E, the reduction data determining unit 711 is able to read and obtain the data mount reduction period corresponding to the type of the shape holding unit 1100 from the ROM 741.

As described above, in this embodiment, the reduction data determining unit 711 is able to determine the data amount reduction periods corresponding to the individual acoustic wave receiving elements only if the information based on the shape of the subject is obtained.

Also in the case illustrated in FIG. 4B, the portions corresponding to distances $d1\_b$ to $d8\_b$ between the plurality of acoustic wave receiving elements 300-1 to 300-8 and the shape holding unit 1100-2 are regarded as data amount reduction regions. In the case illustrated in FIG. 4C, the portions corresponding to distances $d1\_c$ to $d8\_c$ between the plurality of acoustic wave receiving elements 300-1 to 300-8 and the shape holding unit 1100-3 are regarded as data amount reduction regions. In this way, the reduction data determining unit 711 determines the data amount reduction periods in the case of FIG. 4B or FIG. 4C on the basis of the information that is based on the shape of the subject E.

As can be seen in FIGS. 4A to 4C, the data amount reduction regions vary in accordance with the shape of the subject E. That is, the reduction data determining unit 711 changes data amount reduction periods in accordance with the shape of the subject E.

An embodiment of the present invention is not limited to the method of individually setting data amount reduction regions for the plurality of acoustic wave receiving elements 300-1 to 300-8. Any other methods may be adopted as long as the amount of data can be reduced in accordance with the shape of the subject.

For example, in FIG. 4C, the reduction data determining unit 711 may determine the data amount reduction periods corresponding to the plurality of acoustic wave receiving elements 300 on the basis of the shortest distance among the distances from the plurality of acoustic wave receiving elements 300 to the surface of the subject E. That is, the reduction data determining unit 711 may determine a value calculated by dividing the distance $d1\_c$ by a sonic speed in the acoustic matching material 1300 to be the data amount reduction period corresponding to the plurality of acoustic wave receiving elements 300. According to the data amount reduction periods determined in this manner, at least a reception signal of photoacoustic waves generated in the subject is not a target for which the data amount is reduced, and thus an increase in S/N ratio in the subject is not hindered.

Alternatively, the plurality of acoustic wave receiving elements 300 may be grouped into several groups, and data amount reduction periods may be assigned to the individual groups. For example, the acoustic wave receiving elements 300-1 and 300-2 close to each other may be grouped into group 1, the acoustic wave receiving elements 300-3 and 300-4 may be grouped into group 2, the acoustic wave receiving elements 300-5 and 300-6 may be grouped into group 3, and the acoustic wave receiving elements 300-7 and 300-8 may be grouped into group 4.

The data amount reduction period may vary among the measurement positions of the supporting member 400.

A CPU 731 serving as the control unit 730 may set the position of the supporting member 400 in the X, Y, and Z directions so that the highly-sensitive region G is formed inside the subject E on the basis of the shape information about the subject E. The position and size of the highly-sensitive region G are determined in accordance with the arrangement of the plurality of acoustic wave receiving elements 300. Thus, the CPU 731 sets the position of the supporting member 400 so that the highly-sensitive region G is formed inside the subject E on the basis of the shape information about the subject E, and the information about the arrangement of the plurality of acoustic wave receiving elements on the supporting member 400. Information about the size and position of the highly-sensitive region G determined based on the arrangement of the plurality of acoustic wave receiving elements 300 may be stored in the ROM 741 in advance. In this case, the CPU 731 may set a measurement position on the basis of the information about the size and position of the highly-sensitive region G read from the ROM 741 and the shape information about the subject E.

The position of the supporting member 400 may be set so that the center of the highly-sensitive region G is inside the subject E. That is, in this embodiment, a measurement position may be set so that the subject E exists at the curvature center of the hemispherical supporting member 400 at each measurement position.

As a result of setting a measurement position in the above-described manner, photoacoustic waves generated in the subject E can be received with high sensitivity.

S300: Step of Obtaining Reception Signal Data Reduced by Data Amount of Reception Signals Corresponding to Data Amount Reduction Period The scanner 500 causes the supporting member 400 to be located at the measurement position set in step S200. Position information about the supporting member 400 at the measurement position is transmitted to the computer 700 and is stored in the ROM 741 as measurement position information. Alternatively, the measurement position information may be known before measurement is started.

The CPU 731 outputs a control signal so that the light source 100 generates light when the supporting member 400 is located at the measurement position. The light is led by the optical system 200 and is applied to the subject E via the acoustic matching material 1300. The light applied to the subject E is absorbed into the subject E, and thereby photoacoustic waves are generated.

The plurality of acoustic wave receiving elements 300 receive photoacoustic waves generated in the subject E and propagated through the acoustic matching material 1300, and convert the photoacoustic waves into electric signals as time-series reception signals. Subsequently, the signal data obtaining unit 710 stores data obtained by subtracting a reception signal of photoacoustic waves derived from data amount reduction regions from time-series reception signals of photoacoustic waves on the basis of the information about the data amount reduction periods corresponding to the plurality of acoustic wave receiving elements 300 set in step S200.

The signal data obtaining unit 710 is able to reduce the data amount of reception signals of photoacoustic waves derived from the data amount reduction regions by not storing reception signals in the data amount reduction periods.

Alternatively, the signal data obtaining unit 710 may reduce the data amount of reception signals of photoacoustic waves derived from the data amount reduction regions by setting a sampling frequency for reception signals in data amount reduction periods to be lower than a sampling frequency for other reception signals. Even in the case of using a method for reducing a data amount by decreasing a sampling frequency, subject information can be obtained for a region other than the subject from reception signal data although the resolution is low. Thus, the state of a region other than the subject can be checked while reducing the amount of data stored in the memory.

Any other reduction methods may be used as long as the data amount of reception signals of photoacoustic waves received in a data amount reduction period can be reduced.

Hereinafter, a description will be given of a specific example of a method for not storing reception signals in a data amount reduction period on the basis of the information about the data amount reduction period.

The plurality of acoustic wave receiving elements 300-1 to 300-8 illustrated in FIG. 5 receive photoacoustic waves, convert the photoacoustic waves into electric signals, and output the electric signals to AD converters (ADCs) 717-1 to 717-8. The ADCs 717-1 to 717-8 sample the electric signals at a certain frequency in accordance with a clock signal output from a system clock (CLK) 713, convert the electric signals into digital signals, and output the digital signals to first-in first-out (FIFO) memories (hereinafter referred to as FIFOs) 716-1 to 716-8. The FIFOs 716-1 to 716-8 store the digital signals output from the ADCs 717-1 to 717-8 in accordance with clock signals output from the system CLK 713 and write enable signals output from a FIFO control unit 712.

Figure 6:
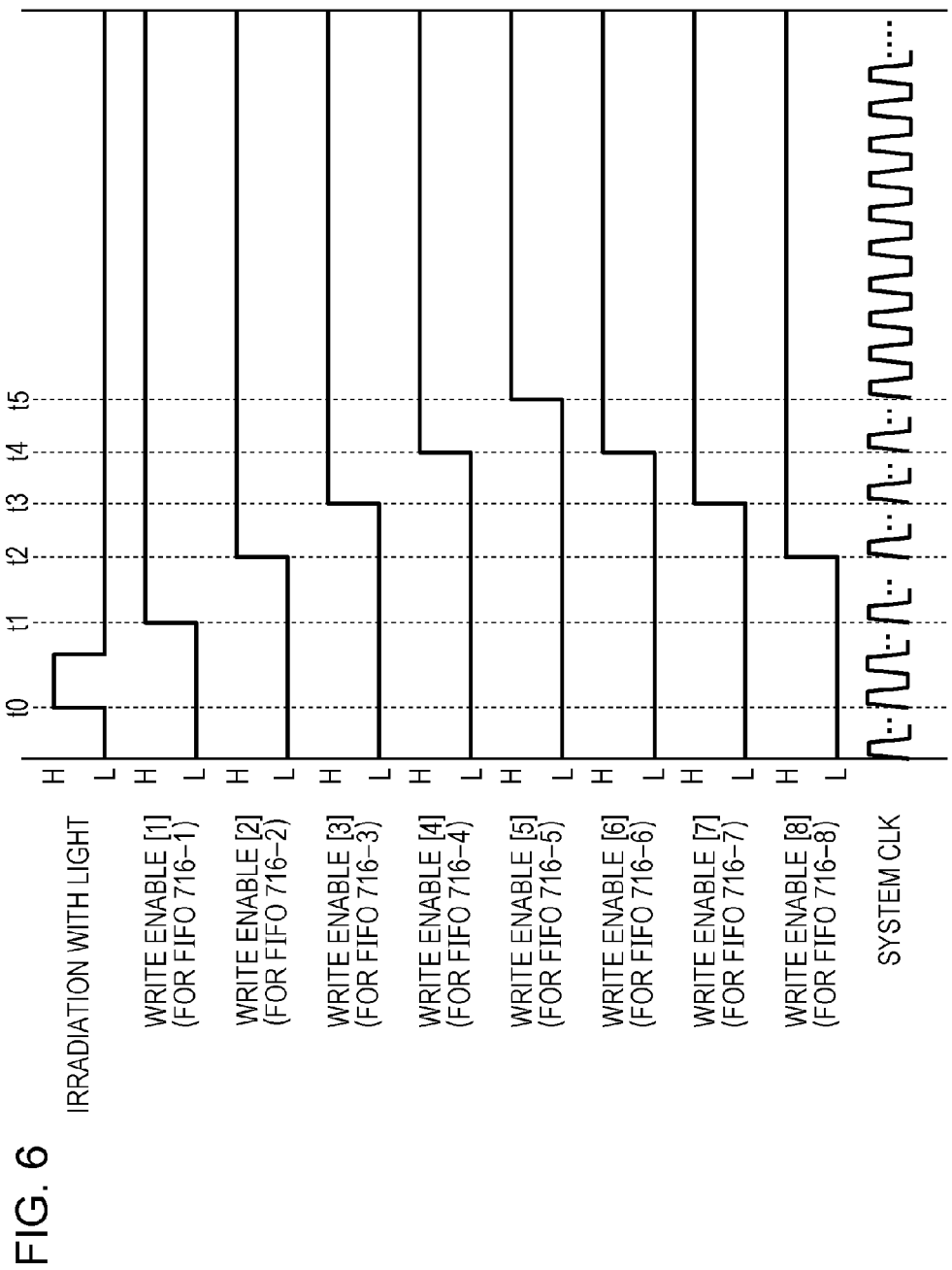
FIG. 6 is a diagram illustrating a write sequence for FIFOs according to the first embodiment.

At this time, the FIFO control unit 712 adjusts output timings of the write enable signals on the basis of the information about the data amount reduction periods for the plurality of acoustic wave receiving elements 300-1 to 300-8. For example, as illustrated in FIG. 6, the FIFO control unit 712 adjusts the output timings of write enable signals [1] to [8] for the FIFOs 716-1 to 716-8. FIG. 6 illustrates that writing for the FIFOs 716-1 to 716-8 is not performed when the level of the write enable signal is L, whereas writing for the FIFOs 716-1 to 716-8 is performed when the level of the write enable signal is H.

That is, in the FIFO 716-1 (the acoustic wave receiving element 300-1), the period from t0 to t1 corresponds to a data amount reduction period. That is, the period from when irradiation with light is started (t=0) to when acoustic waves generated on the surface of a subject reach the acoustic wave receiving element 300-1 (t=1) corresponds to a data amount reduction period. At time t1 and thereafter, photoacoustic waves derived from the subject are received, and thus the write enable signal [1] is set to H, and a digital signal is stored in the FIFO 716-1. In this way, write enable signals are individually given to the FIFOs 716-1 to 716-8 (the acoustic wave receiving elements 300-1 to 300-8). Accordingly, each of the FIFOs 716-1 to 716-8 (the acoustic wave receiving elements 300-1 to 300-8) is able to obtain a digital signal reduced by a reception signal corresponding to a data amount reduction period.

Subsequently, the FIFOs 716-1 to 716-8 transfer, to a dynamic random access memory (DRAM) 718 corresponding to a storage unit in the last stage, the digital signals stored therein in accordance with clock signals output from the system CLK 713 and read enable signals output from the FIFO control unit 712. A selection switch 714 selects one of the FIFOs 716-1 to 716-8 and connects the selected FIFO to the DRAM 718, so that the digital signal is transferred to the DRAM 718. In this way, the DRAM 718 stores, as reception signal data, a digital signal reduced by a reception signal corresponding to a data amount reduction period. The data stored in the DRAM 718 is generated by reducing a reception signal corresponding to a data amount reduction period, and thus the amount of data is reduced. Therefore, according to this embodiment, the DRAM 718 does not need to have a memory capacity for storing all of time-series reception signals, and thus the memory capacity of the DRAM 718 can be reduced. The DRAMs 718 and 722 may be different types of storage media, for example, a static RAM (SRAM) and a flash memory. As the storage media, any types of storage media may be used as long as the capacity, writing speed, and reading speed that do not cause a problem for system operation are ensured.

In this specification, reception signal data is time-series signal data immediately before being used for obtaining subject information by the information obtaining unit 720 described below. That is, reception signal data is time-series signal data stored in the storage unit in the last stage of the signal data obtaining unit 710. Thus, according to this embodiment, the amount of data stored in the storage unit in the last stage of the signal data obtaining unit 710 may be reduced.

For example, the amount of data stored in the storage unit in the last stage may be reduced by reducing the data amount of a reception signal corresponding to a data amount reduction period at the time of transferring reception signals from a storage unit in a preceding stage to a storage unit in a subsequent stage, instead of reducing the amount of data when being stored in the storage unit in the foremost stage.

To reduce the capacities of individual storage units in the signal data obtaining unit 710, the amount of data stored in the storage unit in an initial stage may be reduced. In particular, the amount of data stored in the storage unit in the foremost stage of the signal data obtaining unit 710, that is, the FIFO 716, may be reduced as in this embodiment. As a result of reducing the amount of data in the storage unit in the foremost stage, the amount of data transferred to the following storage unit can be reduced, and thus the time for transferring the data can be shortened.

Further, in this step, in a case where the shape of the subject differs as illustrated in FIGS. 4A to 4C, the data amount of reception signals in the data amount reduction periods corresponding to the individual shapes of subjects can be reduced on the basis of the period determined in step S200.

The transfer destination of the digital signals stored in the storage unit in the foremost stage is not limited to the storage unit in the following stage. The digital signals stored in the storage unit in the foremost stage may be output to an arithmetic unit, preprocessing such as noise processing may be performed on the digital signals by the arithmetic unit, and then the digital signals may be transferred to the storage unit in the following stage.

The reception signal data may be stored in association with position information about the supporting member and information representing the number of irradiations with light. For example, in the case of transferring digital signals from the FIFOs 716-1 to 716-8 to the DRAM 718, a header or a trailer may be attached to the top or end of the digital signal group. The information included in the header or trailer may be the number of the receiving element from which the digital signal group has been obtained, position information about the supporting member, the number of irradiations with light, and a data amount reduction period. Both or one of the header and the trailer may be provided. In the case of providing both of the header and the trailer, the information assigned to each of them may be appropriately determined.

In this embodiment, the amount of data of photoacoustic waves derived from a data amount reduction region is reduced by using write enable signals in FIFOs, but another method may be used. For example, clock signals from the system CLK 713 may be supplied to the ADCs 717-1 to 717-8 only when photoacoustic waves derived from a subject are received. In this case, clock signals from the system CLK 713 are constantly supplied to the FIFOs 716-1 to 716-8. Alternatively, clock signals from the system CLK 713 may be supplied to the FIFOs 716-1 to 716-8 only when photoacoustic waves derived from a subject are received. In this case, clock signals from the system CLK 713 are constantly supplied to the ADCs 717-1 to 717-8. Alternatively, clock signals from the system CLK 713 may be supplied to the ADCs 717-1 to 717-8 and the FIFOs 716-1 to 716-8 only when photoacoustic waves derived from the subject are received. Any other methods may be used as long as the data amount of reception signals of photoacoustic waves derived from a data amount reduction region can be selectively reduced.

S400: Step of Obtaining Subject Information on the Basis of Reception Signal Data The information obtaining unit 720 obtains subject information on the basis of the reception signal data obtained in step S300. That is, a GPU 721 in the information obtaining unit 720 performs processing that is based on an image reconstruction algorithm on the reception signal data stored in the DRAM 718 so as to obtain subject information, and stores the subject information in the DRAM 722.

As described above, the reception signal data obtained in step S300 is data that contributes to subject information of a high S/N ratio about the subject E. Thus, in this step, subject information about the subject E can be obtained with high accuracy. That is, the resolution and quantitativity of the subject information about the subject E obtained in this step are high.

S500: Step of Displaying Subject Information

The display 900 displays the subject information obtained in step S400 in the form of a distribution image or numeric data. For example, the CPU 731 is able to read the subject information from the DRAM 722 and display a distribution image of the subject information on the display 900.

As described above, the photoacoustic apparatus according to this embodiment is able to change, in accordance with the shape of a subject, the period in which the data amount of time-series reception signals output from the plurality of acoustic wave receiving elements 300 is reduced. Accordingly, the data of reception signals of photoacoustic waves derived from a region other than a subject can be selectively reduced even in a case where the shape of the subject differs. That is, the data of reception signals largely contributing to the acquisition of subject information of a high S/N ratio about the subject can be selectively obtained. Accordingly, subject information about the subject can be obtained with high accuracy while reducing the memory capacity by reducing the data amount of reception signals of photoacoustic waves derived from a region other than the subject.

Second Embodiment

Hereinafter, a second embodiment will be described by using the same apparatus as the photoacoustic apparatus according to the first embodiment. The parts described above in the first embodiment are denoted by the same reference numerals, and the detailed description thereof is omitted.

Photoacoustic waves generated as a result of pulsed light emitted from the light source 100 and applied from a surface to a deep portion of the subject E propagate through the subject E and the acoustic matching material 1300, and then reach the plurality of acoustic wave receiving elements 300. The photoacoustic waves generated in the subject propagates in the subject while being affected by frequency dependent attenuation (FDA). For example, FDA in a normal breast is about 0.75 dB/cm/MHz, but photoacoustic waves largely attenuate while propagating through a living body as the frequency of the photoacoustic waves increases. On the other hand, FDA of an acoustic matching material formed of water, gel, or the like is negligible small compared to that of a living body. Thus, in this embodiment, a description will be given without considering attenuation of acoustic waves in the acoustic matching material.

Therefore, in typical cases, as the distance which photoacoustic waves propagate in a subject increases, a high-frequency component of the subject is attenuated more largely by an influence of attenuation of the photoacoustic waves, compared with a low-frequency component. That is, as the distance which photoacoustic waves propagate in the subject increases, a low-frequency component becomes more dominant in the photoacoustic waves received by acoustic wave receiving elements in terms of a frequency band characteristic. A reception signal corresponding to photoacoustic waves including a high-frequency component and having a signal strength decreased due to attenuation of acoustic waves becomes a reception signal that does not largely contribute to increased image quality of the subject. Thus, in this case, there is a low probability of causing decreased image quality of the subject even if an image is generated without using a reception signal corresponding to photoacoustic waves for a high-frequency component.

In a case where the shape of a subject differs, the relative positions of acoustic wave receiving elements and the subject may vary. Thus, the frequency band characteristic of acoustic waves that reach the acoustic wave receiving elements also changes.

Thus, in this embodiment, a sampling frequency is set so that acoustic waves that dominantly include a low-frequency component can be selectively sampled, on the basis of shape information about a subject. Accordingly, the data amount of reception signals corresponding to acoustic waves including a high-frequency component can be reduced.

In a case where the shape of a subject differs, the relative positions of acoustic wave receiving elements and the subject may vary. Thus, a frequency component included in photoacoustic waves received by the acoustic wave receiving elements may also be changed in accordance with the shape of the subject. Thus, in a case where the sampling frequency is not changed when the shape of the subject is changed, the data amount of reception signals of photoacoustic waves including a high-frequency component that could be received with large strength may be reduced.

Operation of Photoacoustic Apparatus

Figure 7:
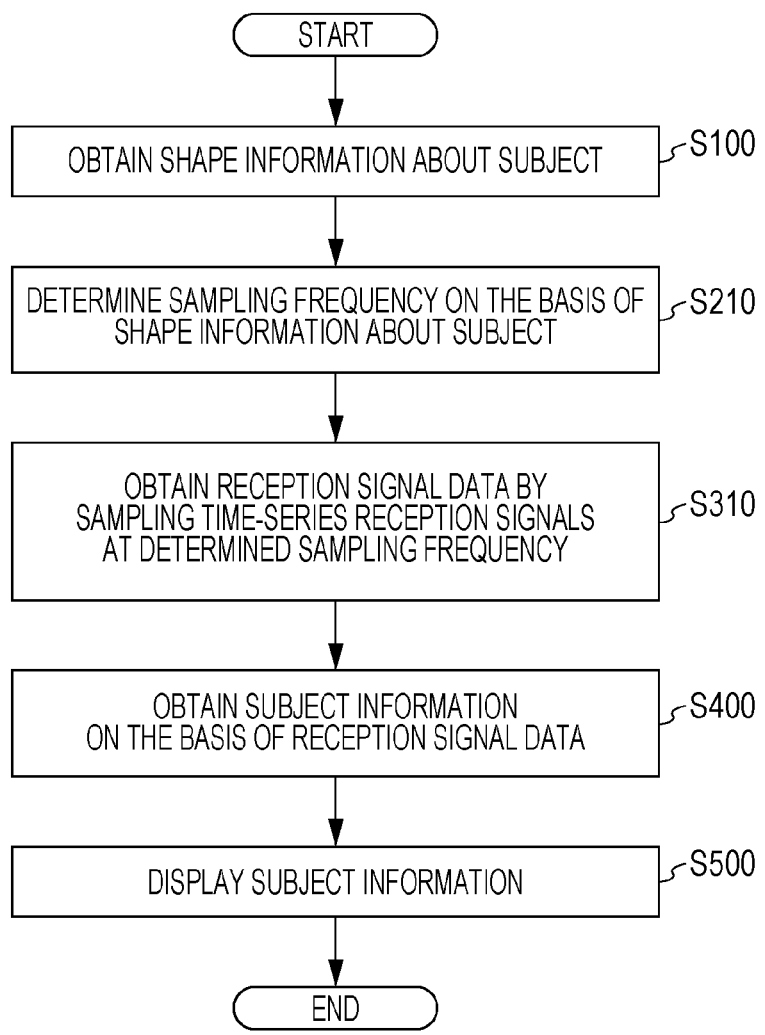
FIG. 7 is a flowchart illustrating an operation of the photoacoustic apparatus according to a second embodiment.

With reference to the flowchart illustrated in FIG. 7, a description will be given of a method for selectively storing reception signals including a frequency component that can be received with large strength. In the flowchart, the same steps as those in FIG. 3 are denoted by the same numerals, and the detailed description thereof is omitted.

S210: Step of Determining Sampling Frequency on the Basis of Information Based on Shape of Subject The signal data obtaining unit 710 determines sampling frequencies corresponding to the plurality of acoustic wave receiving elements 300 on the basis of the information that is based on the shape of the subject E obtained in step S100.

Hereinafter, a description will be given of a method for determining sampling frequencies corresponding to the plurality of acoustic wave receiving elements 300.

Figure 8A:
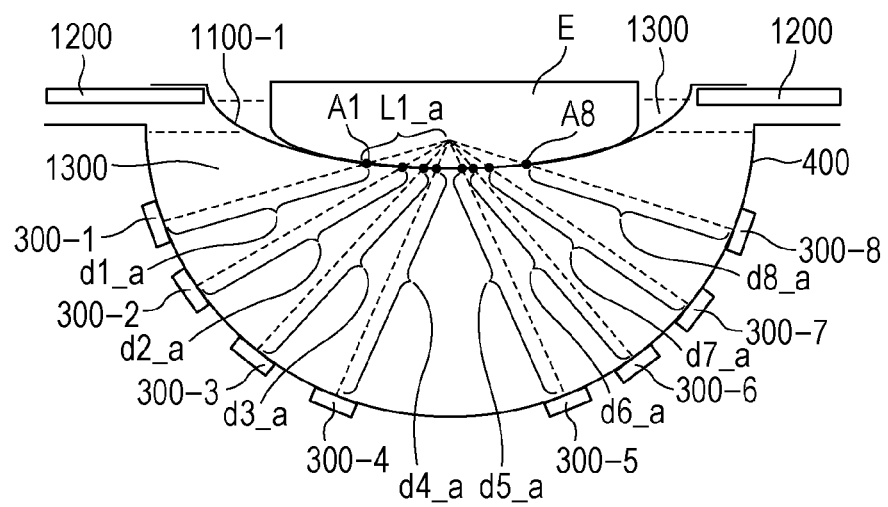
FIGS. 8A and 8B are diagrams illustrating measurement states according to the second embodiment.

In the case of using the plurality of acoustic wave receiving elements 300 arranged as illustrated in FIG. 8A, photoacoustic waves generated at a curvature center X (the center of a highly-sensitive region) of the supporting member at which the orientations of the individual elements converge can be received with high sensitivity. On the other hand, the distances from the surface of the subject to the curvature center X viewed from the individual acoustic wave receiving elements 300 to the curvature center X are different from one another. In this case, a distance $LN\_a$ (N=1 to 8) from the surface of the subject to the curvature center X viewed from an acoustic wave receiving element 300-N (N=1 to 8) corresponds to the length of a line segment connecting a point AN (N=1 to 8) to the curvature center X. For example, a distance L1 from the surface of the subject to the curvature center X viewed from the acoustic wave receiving element 300-1 corresponds to the length of a line segment connecting a point A1 to the curvature center X. For example, in the case of FIG. 8A, regarding a distance $LN\_a$ (N=1 to 8) from the surface of the subject to the curvature center X viewed from an acoustic wave receiving element 300-N (N=1 to 8), a distance $L4\_a$ is shorter than a distance $L1\_a$. In this case, photoacoustic waves that are generated at the curvature center X and reach the acoustic wave receiving element 300-1 are attenuated more largely than photoacoustic waves that are generated at the curvature center X and reach the acoustic wave receiving element 300-4. In particular, regarding a high-frequency component included in photoacoustic waves, the one that reaches the acoustic wave receiving element 300-1 is attenuated more largely than the one that reaches the acoustic wave receiving element 300-4.

In this step, a sampling frequency differs between an acoustic wave receiving element that receives photoacoustic waves in which a high-frequency component is attenuated to a large extent and a low-frequency component is dominant, and an acoustic wave receiving element that receives photoacoustic waves in which a high-frequency component is attenuated to a small extent. For example, a sampling frequency in the acoustic wave receiving element 300-1, which receives photoacoustic waves in which a high-frequency component is attenuated to a large extent, is set to be lower than a sampling frequency in the acoustic wave receiving element 300-4, which receives photoacoustic waves in which a high-frequency component is attenuated to a small extent. In the acoustic wave receiving element 300-1, in which the sampling frequency is low, photoacoustic waves including a high-frequency component are not faithfully sampled, and photoacoustic waves including a low-frequency component are selectively sampled. On the other hand, with the sampling frequency being lowered, the amount of reception signal data corresponding to the acoustic wave receiving element 300-1 is smaller than the amount of reception signal data corresponding to the acoustic wave receiving element 300-4. However, the photoacoustic waves including a high-frequency component that reach the acoustic wave receiving element 300-1 have a decreased signal strength due to the attenuation, and correspond to data that does not largely contribute to increased image quality for the subject E. Thus, there is a low probability that image quality for a subject decreases because photoacoustic waves including a high-frequency component are not faithfully sampled.

The reduction data determining unit 711 is able to selectively store a frequency component that has reached an acoustic wave receiving element with large strength, by setting a sampling frequency in the above-described manner on the basis of the information that is based on the shape of the subject obtained in step S100.

An amount of attenuation $\Delta I$ [dB] in a case where photoacoustic waves of a certain frequency f [MHz] propagate by a depth L [cm] in a subject having FDA of $\alpha$ [dB/cm/MHz] is expressed by equation (1).

$$\Delta I = \alpha \cdot L \cdot f \qquad \text{equation (1)}$$

Here, a permissible amount of attenuation in a case where the sound pressure at the time of generation of photoacoustic waves is decreased to be lower than an S/N ratio that largely contributes to increased image quality is represented by $\Delta I'$. In this case, a reception signal of photoacoustic waves of a frequency higher than the frequency f expressed by equation (2) is likely to be a frequency component that does not largely contribute to increased image quality.

$$f = \frac{\Delta I'}{\alpha \cdot L} \qquad \text{equation (2)}$$

The reduction data determining unit 711 is able to sufficiently sample frequency components of a frequency f or less, by sampling time-series reception signals at a sampling frequency with which the frequency f determined by equation (2) can be sufficiently sampled. That is, frequency components that largely contribute to increased image quality can be sampled at a sufficient sampling frequency, whereas faithful sampling is not performed on frequency components that do not largely contribute to increased image quality, so as to reduce the amount of data.

For example, $\Delta I'$ may be set so as to obtain an S/N ratio that does not largely contribute to increased image quality in a case where the sound pressure at the time of generation of photoacoustic waves is attenuated by 10 dB or more. If $\Delta I'$ is set to a small value, there is a probability that frequency components that largely contribute to increased image quality are not faithfully sampled, and thus $\Delta I'$ may be set to 5 dB or more. That is, $\Delta I'$ may be set to 5 dB or more and 10 dB or less. Further, $\Delta I'$ may be appropriately set in accordance with the minimum reception sound pressure of an acoustic wave receiving element. Further, a user is able to input and set a value of $\Delta I'$ by using the input unit 1000.

FDA can be appropriately set by using the input unit 1000, in accordance with the type of subject. In a case where the type of subject is known in advance, a value of FDA may be stored in advance in the ROM 741 serving as the storage unit 740.

Typically, a sampling frequency may be set so that a frequency determined by using equation (2) in accordance with a sampling theorem can be sufficiently sampled. For example, a sampling frequency may be twice or more the frequency f determined by using equation (2).

However, the amount of reception signal data increases as the sampling frequency increases, and thus it is not desirable to increase the sampling frequency without limit. As a result of earnest studies, the inventors have found that, in the photoacoustic apparatus, a sampling frequency that is ten times or more the frequency f does not largely contribute to an increase in reproducibility of data. Also, the inventors have found that a component of the frequency f can be sufficiently sampled at a sampling frequency that is about four times the frequency f. Thus, the sampling frequency may be ten times or less the frequency f. Also, in order to reduce the data amount of reception signals, the sampling frequency may be four times or less the frequency f.

Specifically, the sampling frequency may be twice or more the frequency f and ten times or less the frequency f. Further, in order to reduce the data mount of reception signals, the sampling frequency may be twice or more the frequency f and four times or less the frequency f.

For example, a case where the reduction data determining unit 711 receives position coordinate information about the surface of the subject E as information based on the shape of the subject is discussed. In this case, the reduction data determining unit 711 calculates the distances L1_a to L8_a on the basis of the position coordinates of the surface of the subject E, the position coordinates of the plurality of acoustic wave receiving elements 300, and the position coordinates of the curvature center X.

Subsequently, the reduction data determining unit 711 obtains sampling frequencies corresponding to the plurality of acoustic wave receiving elements 300 on the basis of the information representing the distances L1_a to L8_a by using equation (2).

Typically, the arrangement of the plurality of acoustic wave receiving elements 300 is known in advance, and thus the position coordinate information about the individual elements can be stored in the ROM 741 in advance. Thus, the reduction data determining unit 711 is able to use the position coordinate information about the individual elements to calculate the distances by reading the information from the ROM 741.

Further, the shape of the shape holding unit 1100 is known in advance in addition to the arrangement of the plurality of acoustic wave receiving elements 300. Thus, sampling frequencies corresponding to individual shapes (types) of the shape holding unit 1100 can be calculated in advance and stored in the ROM 741. That is, in a case where the reduction data determining unit 711 receives information about the type of the shape holding unit 1100 as the information based on the shape of the subject E, the reduction data determining unit 711 is able to read and obtain the sampling frequency corresponding to the type of the shape holding unit 1100 from the ROM 741.

As described above, in this embodiment, the reduction data determining unit 711 is able to determine the sampling frequencies corresponding to the individual acoustic wave receiving elements only by obtaining information that is based on the shape of the subject.

Figure 8B:
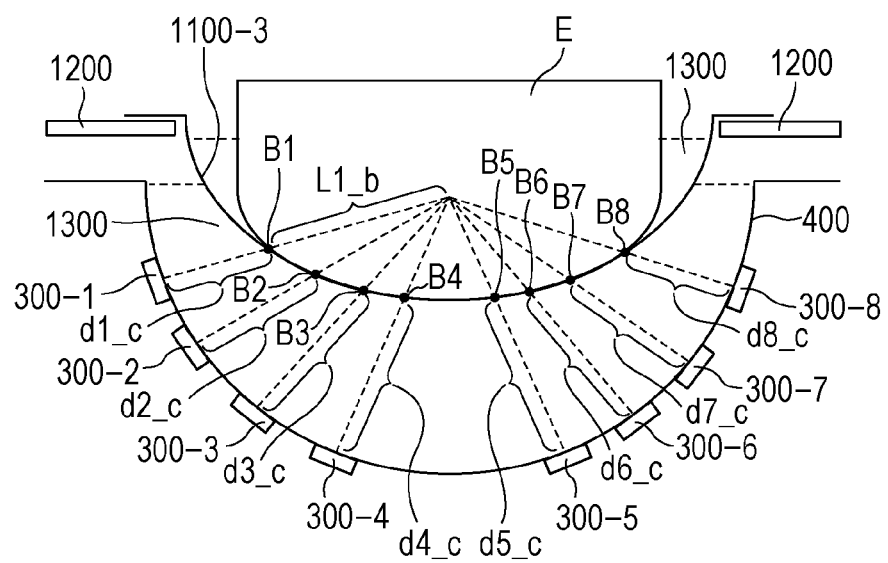

Also in the case of FIG. 8B, the reduction data determining unit 711 determines the sampling frequencies corresponding to the plurality of acoustic wave receiving elements 300 on the basis of the information that is based on the shape of the subject E in the case of FIG. 8B.

In this way, the reduction data determining unit 711 is able to appropriately determine sampling frequencies in accordance with the shape of the subject, even if the shape of the subject is different.

In this embodiment, sampling frequencies for selectively reducing the data amount of reception signals corresponding to attenuated components among components included in photoacoustic waves generated at the curvature center of the supporting member 400 are set. In this step, it is also possible to set sampling frequencies for selectively reducing the data amount of reception signals corresponding to attenuated components among components included in photoacoustic waves generated at a certain position other than the curvature center of the supporting member 400.

An embodiment is not limited to the method of individually setting sampling frequencies for the plurality of acoustic wave receiving elements 300-1 to 300-8. Any other methods may be adopted as long as the data amount of a specific frequency component can be reduced in accordance with the shape of a subject.

For example, in FIG. 8A, the reduction data determining unit 711 may determine a sampling frequency on the basis of the shortest distance among the distances from the curvature center X to the surface of the subject E viewed from the plurality of acoustic wave receiving elements 300 to the curvature center X. That is, the reduction data determining unit 711 may determine a sampling frequency calculated on the basis of the distance $L4\_a$ to be a sampling frequency corresponding to the plurality of acoustic wave receiving elements 300. With the sampling frequency determined in this manner, at least a high-frequency component of photoacoustic waves that have been generated at the curvature center X and reached the acoustic wave receiving element 300-4 is not regarded as a target for which the amount of data is reduced, and thus degradation of image quality can be prevented.

Alternatively, the plurality of acoustic wave receiving elements 300 may be grouped into several groups, and sampling frequencies may be assigned to the individual groups. For example, elements at almost the same distance from a subject may be grouped together, or elements close to one another may be grouped together.

A description has been given of a method for sampling time-series reception signals at a constant sampling frequency. Alternatively, time-series reception signals output from the individual elements may be sampled by changing a sampling frequency in time series. In a time-series reception signal, photoacoustic waves whose reception timing is typically early are photoacoustic waves generated near the surface of a subject, and thus the degree of attenuation is low. On the other hand, photoacoustic waves whose reception timing is typically late are photoacoustic waves generated at a deep portion of a subject, and thus the degree of attenuation is high. Regarding a high-frequency component, photoacoustic waves generated in a deep portion are largely attenuated compared to a low-frequency component. Thus, the reduction data determining unit 711 is able to selectively reduce the data of an attenuated high-frequency component by decreasing a sampling frequency as the reception timing of a time-series reception signal becomes later. In a case where a constant sampling frequency is set for a time-series reception signal, with the curvature center being a reference position, there is a probability that faithful sampling is not performed on a high-frequency component with a high S/N ratio in photoacoustic waves that are generated near the surface of a subject and are attenuated to a small extent. In contrast, as a result of changing the sampling frequency in time series, a frequency component with a sufficient S/N ratio can be selectively stored at individual reception timings, and the amount of data can be effectively reduced.

Figure 9:
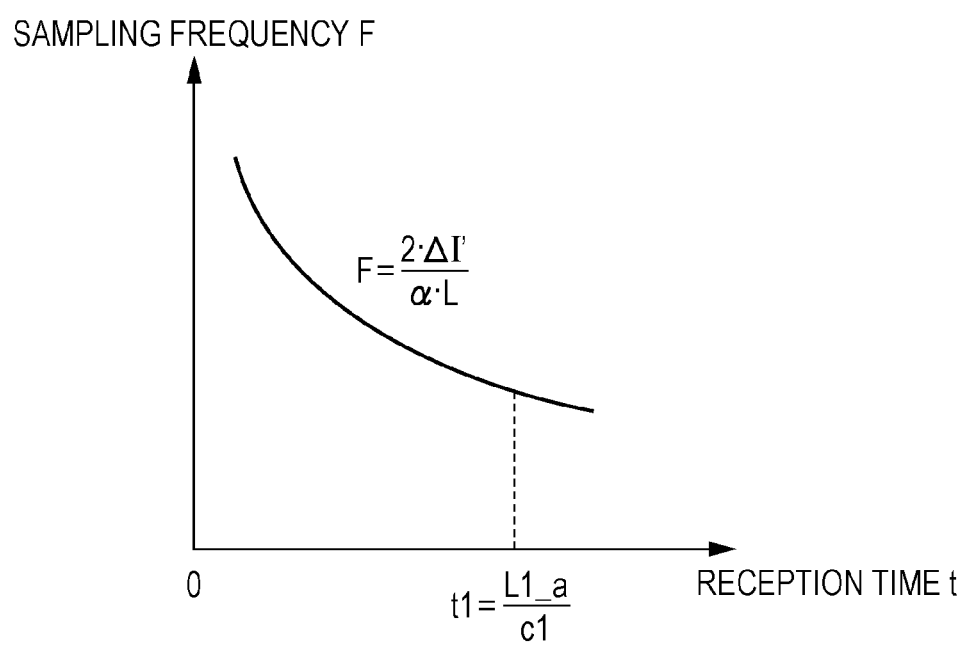
FIG. 9 is a diagram illustrating an example of a sampling frequency according to the second embodiment.

For example, the case of changing the sampling frequency corresponding to the acoustic wave receiving element 300-1 in FIG. 8A in time series is discussed. FIG. 9 illustrates an example of the sampling frequency corresponding to the acoustic wave receiving element 300-1. In FIG. 9, the horizontal axis represents reception time t, and the vertical axis represents sampling frequency F. The timing at which a photoacoustic wave generated on the surface of the subject reaches the acoustic wave receiving element 300-1 is a reception time t=0. Here, the reception time t corresponds to a value calculated by dividing a distance L from the curvature center X to the surface of the subject E by a sonic speed c1 in the subject E.

As described above, photoacoustic waves generated at a deep portion are attenuated more largely, and thus a low-frequency component becomes dominant. Thus, in FIG. 9, the sampling frequency F is decreased as the reception time t becomes later, so that a low-frequency component can be selectively sampled. In FIG. 9, the value that is twice the frequency f calculated by using equation (2) is regarded as the sampling frequency F. For example, a reception signal corresponding to a reception time $t1=L1\_a/c1$ of photoacoustic waves generated at the curvature center X is sampled at a sampling frequency $F=2\Delta I'/\alpha L1\_a$.

In acoustic waves at a reception time t=0, attenuation is not observed, and acoustic waves of any frequency can be received. Thus, the initial value of F (F(0)) can be infinite. Actually, however, an appropriate value that is twice or more the upper limit value of the frequency band targeted by a user can be set as F(0). F(0) may be set as an initial value, and the sampling frequency may be set to the sampling frequency F illustrated in FIG. 9 or more, and a value smaller than F(0) as the reception time t becomes later, and thereby reduction of the amount of data may be achieved.

Instead of changing the sampling frequency for each reception time, a sampling frequency corresponding to a certain reception time may be used as a sampling frequency for a close reception time. That is, the sampling frequency may be changed step by step in time series.

S310: Step of Obtaining Reception Single Data by Sampling a Time-Series Reception Signal at a Determined Sampling Frequency The scanner 500 causes the supporting member 400 to be located at a set position. Position information about the supporting member 400 at the measurement position is transmitted to the computer 700, and is stored as measurement position information in the ROM 741. Alternatively, the measurement position information may be known before measurement is started.

The CPU 731 serving as the control unit 730 outputs a control signal so that the light source 100 generates light when the supporting member 400 is located at the set measurement position. The light is led by the optical system 200, and is applied to the subject E via the acoustic matching material 1300. The light applied to the subject E is absorbed in the subject E, and thereby photoacoustic waves are generated.

The plurality of acoustic wave receiving elements 300 receive the photoacoustic waves generated in the subject E and propagated through the acoustic matching material 1300, and convert the photoacoustic waves into electric signals as time-series reception signals.

Subsequently, the signal data obtaining unit 710 samples a time-series reception signal at the sampling frequency determined in step S210, and stores sampled data as reception signal data.

Hereinafter, a description will be given of a specific example of a method for performing sampling at the sampling frequency determined in step S210 by using the computer 700 illustrated in FIG. 5.

In the signal data obtaining unit 710 illustrated in FIG. 5, information about the sampling frequency that is determined in step S210 and output from the reduction data determining unit 711 is input to the FIFO control unit 712 and the system CLK 713. The FIFO control unit 712 supplies write enable signals [1] to [8] and read enable signals [1] to [8] to the FIFOs 716-1 to 716-8. The system CLK 713 supplies sampling clock signals [1] to [8] to the ADCs 717-1 to 717-8. Further, the system CLK 713 supplies write clock signals [1] to [8] and read clock signals [1] to [8] to the FIFOs 716-1 to 716-8. The FIFO control unit 712 and the system CLK 713 control the state of sampling of the time-series reception signals output from the plurality of acoustic wave receiving elements 300 in accordance with the information about the sampling frequency output from the reduction data determining unit 711.

FIG. 10 is a diagram illustrating the sampling clock signals [1] to [8] and the write clock signals [1] to [8] that are supplied by the system CLK 713 to the ADCs 717-1 to 717-8 and the FIFOs 716-1 to 716-8 in the measurement state illustrated in FIG. 8A. That is, FIG. 10 is a diagram illustrating a sampling sequence that is based on the sampling frequency determined in step S210.

For example, in this embodiment, the sampling frequency is increased from the acoustic wave receiving element 300-1 toward the acoustic wave receiving element 300-4 on the basis of the sampling frequency determined in step S210. On the other hand, the sampling frequency is decreased from the acoustic wave receiving element 300-5 toward the acoustic wave receiving element 300-8.

For the reception signals of photoacoustic waves received by the acoustic wave receiving elements 300-1 and 300-8, sampling is performed by using the sampling clock signals [1] and [8] and the write clock signals [1] and [8] of the same frequency. For the reception signals of photoacoustic waves received by the acoustic wave receiving elements 300-2 and 300-7, sampling is performed by using the sampling clock signals [2] and [7] and the write clock signals [2] and [7] of the same frequency. For the reception signals of photoacoustic waves received by the acoustic wave receiving elements 300-3 and 300-6, sampling is performed by using the sampling clock signals [3] and [6] and the write clock signals [3] and [6] of the same frequency. For the reception signals of photoacoustic waves received by the acoustic wave receiving elements 300-4 and 300-5, sampling is performed by using the sampling clock signals [4] and [5] and the write clock signals [4] and [5] of the same frequency.

In this specification, reception signal data is time-series signal data immediately before being used for obtaining subject information by the information obtaining unit 720 described below, that is, time-series signal data stored in the storage unit in the last stage of the signal data obtaining unit 710. Thus, according to this embodiment, the data stored in the storage unit in the last stage of the signal data obtaining unit 710 may be sampled at the sampling frequency determined in step S210.

For example, in the stage of being stored in the storage unit in the foremost stage, the data may be sampled at a certain sampling frequency, and the data may be resampled at the sampling frequency determined in step S210 when being transferred from the storage unit in the foremost stage to the storage unit in the following stage. Also in this case, the amount of reception signal data stored in the storage unit in the last stage can be reduced.

To reduce the capacities of individual storage units in the signal data obtaining unit 710, the amount of data stored in the storage unit in an initial stage may be reduced. In particular, as in this embodiment, the amount of data may be reduced by sampling it at the sampling frequency determined in step S210 before the data is stored in the storage unit in the foremost stage of the signal data obtaining unit 710, that is, the FIFO 716. Alternatively, a sampling clock signal may be set to a certain frequency $f_H$, and a write enable signal of the FIFO 716 may be set to H for one cycle every N clock cycle, so that the sampling frequency may be substantially set to $f_H/N$. In this way, with the amount of data being reduced in a storage unit in an initial stage, the amount of data transferred to the following storage unit can be reduced, and accordingly the time for transferring the data can be shortened.

In this step, also in a case where the shape of a subject is different as illustrated in FIGS. 4A to 4C, time-series reception signals can be sampled at sampling frequencies corresponding to the individual shapes of subjects, and the amount of data can be reduced.

The transfer destination of a digital signal obtained by the storage unit in the foremost stage is not limited to the storage unit in the following stage. That is, the digital signal obtained by the storage unit in the foremost stage may be output to an arithmetic unit, preprocessing such as noise processing may be performed on the digital signal by the arithmetic unit, and the digital signal may be transferred to the storage unit in the following stage.

The reception signal data may be stored in association with position information about the supporting member and information representing the number of irradiations with light.

Control similar to that according to this embodiment can be realized by using a random access memory (RAM) instead of a FIFO.

In this step, the processing of reducing the amount of reception signal data generated in a region other than the subject may be performed, as in the first embodiment.

As long as a reception signal including a target frequency component can be selectively and appropriately sampled, any method may be used to obtain reception signal data with respect to time-series reception signals received by the plurality of acoustic wave receiving elements 300.

S400: Step of Obtaining Subject Information on the Basis of Reception Signal Data The information obtaining unit 720 obtains subject information on the basis of the reception signal data obtained in step S310. That is, the GPU 721 of the information obtaining unit 720 obtains subject information by performing processing that is based on an image reconstruction algorithm on the reception signal data stored in the DRAM 718, and stores the subject information in the DRAM 722.

As described above, the reception signal data obtained in step S310 is data corresponding to a frequency component of photoacoustic waves that have reached an acoustic wave receiving element with large strength among photoacoustic waves generated in the subject. Thus, in this step, subject information with a high S/N ratio can be obtained compared to the case of obtaining subject information by using a frequency component of photoacoustic waves with small strength.

S500: Step of Displaying Subject Information

The display 900 displays the subject information obtained in step S400 in the form of a distribution image or numeric data. For example, the CPU 731 is able to read the subject information from the DRAM 722 and display the distribution image of the subject information on the display 900.

As described above, the photoacoustic apparatus according to this embodiment is able to change a sampling frequency that is used for sampling time-series reception signals output from the plurality of acoustic wave receiving elements 300 in accordance with the shape of a subject. Accordingly, even if the shape of a subject differs, the data amount of reception signals including an attenuated frequency component included in photoacoustic waves can be selectively reduced. That is, reception signals that contribute to obtain subject information of a high S/N ratio can be selectively obtained. Thus, the data amount of an attenuated frequency component included in photoacoustic waves can be reduced, and thus the capacity of a memory for storing reception signal data can be reduced.

In an embodiment of the present invention, a data amount reduction period may be set in units of distances or times. Alternatively, a data amount reduction period may be set in units of the number of sampling clock signals of an ADC, the number of system CLK signals, or the number of pieces of data. Any method may be used to set a data amount reduction period as long as a region can be designated.

In the embodiments of the present invention, the number of acoustic wave receiving elements is eight. The number of acoustic wave receiving elements is not limited to eight, and any number of acoustic wave receiving elements may be used in accordance with the specifications of the apparatus.

The end timing of a data acquisition period may be set to be the same among all the acoustic wave receiving elements, or may be individually set for the individual acoustic wave receiving elements.

In the case of individually setting an end timing of a data acquisition period for the individual acoustic wave receiving elements, a region where a subject does not exist on a directional axis of individual receiving elements may be determined on the basis of shape information about the subject, and the determination result may be reflected in the end timing of the data acquisition period.

The embodiments of the present invention have been described above. The above-described embodiments are merely examples from all points of view, and do not limit the scope of the present invention.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to embodiments, it is to be understood that the invention is not limited to the disclosed embodiments. The scope of the following claims is to be accorded the broadest interpretation so as to encompass all such modifications and equivalent structures and functions.

This application claims the benefit of Japanese Patent Application No. 2014-100851, filed May 14, 2014, which is hereby incorporated by reference herein in its entirety.

What is claimed is:

1. An apparatus comprising:
   a light source;
   a receiving element configured to receive, at a plurality of positions, a photoacoustic wave generated through irradiation of a subject with single pulsed light generated by the light source and output a time-series reception signal corresponding to the single pulsed light; and
   a signal data obtaining unit configured to:
   obtain the time-series reception signal output from the receiving element;
   generate reception signal data from the time-series reception signal, and
   store the reception signal data,
   wherein the signal data obtaining unit is configured to obtain information on a shape of the subject and determine a first period corresponding to a period in which the receiving element receives a photoacoustic wave generated in a region other than the subject and a second period corresponding to a period in which the receiving element receives a photoacoustic wave generated in the subject on the basis of the information on the shape of the subject, and wherein the signal data obtaining unit is configured to generate the reception signal data in such a manner that a data amount per unit of time of the time-series reception signal which is output from the receiving element in the first period and is stored in the signal data obtaining unit is smaller than a data amount per unit of time of the time-series reception signal which is output from the receiving element in the second period and is stored in the signal data obtaining unit.

2. The apparatus according to claim 1, further comprising:

an attachment unit to which one of a plurality of holding units is attachable in a replaceable manner, the plurality of holding units each having a different shape such that each of the holding units is capable of holding the shape of a differently shaped subject, wherein the signal data obtaining unit:

stores a plurality of periods corresponding to the plurality of holding units, obtains, as the information on the shape of the subject, information on a type of the holding unit attached to the attachment unit among the plurality of holding units, and selects the first period corresponding to the holding unit attached to the attachment unit from among the plurality of periods on the basis of the information on the type of the holding unit attached to the attachment unit.

3. The apparatus according to claim 2, wherein the signal data obtaining unit obtains the information on the type of the holding unit output from an input unit configured to allow the type of the holding unit attached to the attachment unit to be input.

4. The apparatus according to claim 1, further comprising:

a plurality of receiving elements configured to receive the photoacoustic wave at the plurality of positions and output a plurality of time-series reception signals corresponding to the plurality of receiving elements and the pulsed light with which the subject is irradiated once, wherein the signal data obtaining unit generates a plurality of pieces of reception signal data by determining the first period corresponding to each of the plurality of time-series reception signals in different periods, and stores the plurality of pieces of reception signal data.

5. The apparatus according to claim 1, wherein the signal data obtaining unit determines a sampling frequency on the basis of the information that is based on the shape of the subject, generates the reception signal data by sampling the time-series reception signal in the first period at a first sampling frequency, and sampling the time-series reception signal in the second period at a second sampling frequency larger than the first sampling frequency.

6. The apparatus according to claim 5, wherein the signal data obtaining unit determines the first or second sampling frequency on the basis of the information that is based on the shape of the subject.

7. The apparatus according to claim 5, further comprising:

an attachment unit to which one of a plurality of holding units is attachable in a replaceable manner, the plurality of holding units each having a different shape such that each of the holding units is capable of holding the shape of a differently shaped subject, wherein the signal data obtaining unit:

stores a plurality of sampling frequencies, obtains information on the type of the holding unit attached to the attachment unit among the plurality of holding units as the information on the shape of the subject, selects a sampling frequency corresponding to the holding unit attached to the attachment unit as the first or second sampling frequency from among the plurality of sampling frequencies on the basis of the information on the type of the holding unit attached to the attachment unit, and generates the reception signal data by sampling the time-series reception signal at the selected sampling frequency, and stores the reception signal data.

8. The apparatus according to claim 7, wherein the signal data obtaining unit obtains the information on the type of the holding unit output from an input unit configured to allow the type of the holding unit attached to the attachment unit to be input.

9. The apparatus according to claim 4, wherein directional axes of at least some of the plurality of receiving elements converge.

10. An apparatus comprising:

a light source;

a receiving element configured to receive, at a plurality of positions, a photoacoustic wave generated through irradiation of a subject with single pulsed light generated by the light source and output a time-series reception signal corresponding to the single pulsed light; and a signal data obtaining unit configured to:

obtain the time-series reception signal output from the receiving element;

generate reception signal data from the time-series reception signal, and store the reception signal data, wherein the signal data obtaining unit:

obtains information on a shape of the subject, determines a first period corresponding to a period in which the receiving element receives a photoacoustic wave generated in a region other than the subject and a second period corresponding to a period in which the receiving element receives a photoacoustic wave generated in the subject on the basis of the information on the shape of the subject, stores the time-series reception signal corresponding to the single pulsed light which is output from a receiving element in the second period as the reception signal data and does not store the time-series reception signal which is output from the receiving element in the first period.

11. The apparatus according to claim 10, further comprising:

a plurality of receiving elements configured to receive the photoacoustic wave at the plurality of positions and output a plurality of time-series reception signals corresponding to the plurality of receiving elements and the single pulsed light, wherein the signal data obtaining unit generates a plurality of pieces of reception signal data by determining the first period corresponding to each of the plurality of series reception signals in different periods, and stores the plurality of pieces of reception signal data.

12. A method comprising:
irradiating a subject with single pulsed light;
receiving, at a plurality of positions, a photoacoustic wave generated through irradiation of the subject with the single pulsed light;
obtaining a time-series reception signal corresponding to the single pulsed light output by receiving the photoacoustic wave;
obtaining information on a shape of the subject;
determining a first period corresponding to a period in which a photoacoustic wave generated in a region other than the subject is received and a second period corresponding to a period in which a photoacoustic wave generated in the subject is received on the basis of the information on the shape of the subject;
generating reception signal data from the time-series reception signal; and
storing the reception signal data, and
wherein, in generating the reception signal data, a data amount per unit of time of the time-series reception signal which is obtained by receiving the photoacoustic wave in the first period and is stored is smaller than a data amount per unit of time of the time-series reception signal which is obtained by receiving the photoacoustic wave in the second period and is stored.

13. A method comprising:
irradiating a subject with single pulsed light;
receiving, at a plurality of positions, a photoacoustic wave generated through irradiation of the subject with the single pulsed light;
obtaining a time-series reception signal corresponding to the single pulsed light output by receiving the photoacoustic wave;
obtaining information on a shape of the subject;
determining a first period corresponding to a period in which a photoacoustic wave generated in a region other than the subject is received and a second period corresponding to a period in which a photoacoustic wave generated in the subject is received on the basis of the information on the shape of the subject; and
storing the time-series reception signal which is output from a receiving element in the second period as reception signal data and not storing the time-series reception signal which is output from the receiving element in the first period.

14. The apparatus according to claim 1, further comprising an information obtaining unit configured to obtain information on the subject on the basis of the reception signal data stored in the signal data obtaining unit.

\* \* \* \* \*